United States Patent [19]

Van Loveren et al.

[11] Patent Number: 4,605,165

[45] Date of Patent: * Aug. 12, 1986

[54] CONSTANT RATE VOLATILE COMPOSITION DISPENSING ARTICLE AND PROCESS FOR USING SAME

[75] Inventors: Augustinus G. Van Loveren, Rye; Marina A. Munteanu, New York, both of N.Y.; Geoffrey B. Seaber, Ijsselstein, Netherlands

[73] Assignee: International Flavors & Fragrances Inc., New York, N.Y.

[*] Notice: The portion of the term of this patent subsequent to Jun. 14, 2000 has been disclaimed.

[21] Appl. No.: 620,167

[22] Filed: Jun. 13, 1984

[51] Int. Cl.$^4$ .................. A61L 9/04; A61L 9/01; A61L 9/12
[52] U.S. Cl. ............................ 239/6; 239/56; 239/60
[58] Field of Search .................. 239/6, 34, 55–57, 239/60

[56] References Cited

U.S. PATENT DOCUMENTS

| | | | |
|---|---|---|---|
| 3,770,199 | 11/1973 | Hoek et al. | 239/54 |
| 3,844,865 | 10/1974 | Elton et al. | 156/229 |
| 3,870,593 | 3/1975 | Elton et al. | 161/159 |
| 3,885,737 | 5/1975 | Watkins | 239/34 |
| 4,014,501 | 3/1977 | Buckenmayer | 239/58 |
| 4,130,245 | 12/1978 | Bryson | 239/34 |
| 4,145,001 | 3/1979 | Weyenberg et al. | 239/56 |
| 4,161,283 | 7/1979 | Hyman | 239/55 |
| 4,226,944 | 10/1980 | Stone et al. | 239/60 |
| 4,227,024 | 10/1980 | Spector | 239/36 |
| 4,247,498 | 1/1981 | Castro | 264/28 |
| 4,248,380 | 2/1981 | Lee et al. | 239/53 X |
| 4,285,468 | 8/1981 | Hyman | 239/55 |
| 4,330,416 | 5/1982 | Sprecker | 252/8.9 |
| 4,387,849 | 6/1983 | Van Loveren et al. | 239/60 |
| 4,440,819 | 4/1984 | Rosser et al. | 428/273 X |
| 4,452,845 | 6/1984 | Lloyd et al. | 428/220 |

FOREIGN PATENT DOCUMENTS

| | | |
|---|---|---|
| 1922783 | 5/1984 | Australia. |
| 1021916 | 12/1977 | Canada. |
| 1039911 | 10/1978 | Canada. |
| 0046071 | 2/1982 | European Pat. Off.. |
| 0107915 | 9/1984 | European Pat. Off.. |
| 55-81655 | 6/1980 | Japan. |
| 55-36515 | 9/1980 | Japan. |
| 59-6059 | 1/1984 | Japan. |
| 1226841 | 3/1971 | United Kingdom. |
| 1414785 | 11/1975 | United Kingdom. |
| 2081721 | 2/1982 | United Kingdom. |

*Primary Examiner*—Andres Kashnikow
*Attorney, Agent, or Firm*—Arthur L. Liberman

[57] ABSTRACT

Described is an article useful for dispensing at a constant rate, continuously or discontinuously for discrete periods of time a volatile composition of matter such as an air freshener or perfume composition into the atmosphere surrounding said article, the article being a hollow totally enclosed flexible, rigid or partially flexible-partially rigid structure comprising a thin shell totally enclosing an inner void with part of the thin shell comprising a microporous polymer containing a plurality of finite solid filler particles whereby when the article is located in the ambient environment, the volatile material molecules are transported through the porous polymer at a substantially constant mass flow rate both of the individual volatile components and totally through the porous polymer. The functioning of the article is enabled because the microporous polymer section has (i) the property of transporting water vapor at a rate of between 50 up to 1000 g/m$^2$/day at about 25° C. and at about 50% relative humidity at about atmospheric pressure and having an air transport rate of 100–20,000 Gurley seconds and a thickness in the range of from about 0.01 mils up to about 20 mils.

12 Claims, 47 Drawing Figures

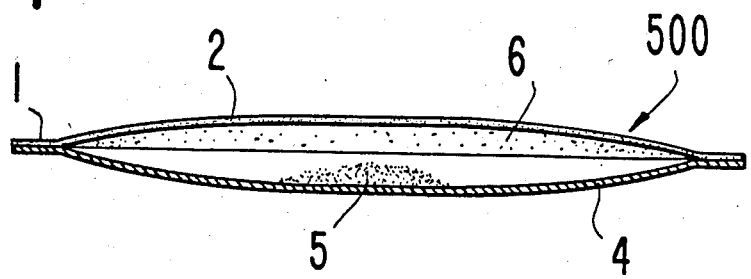
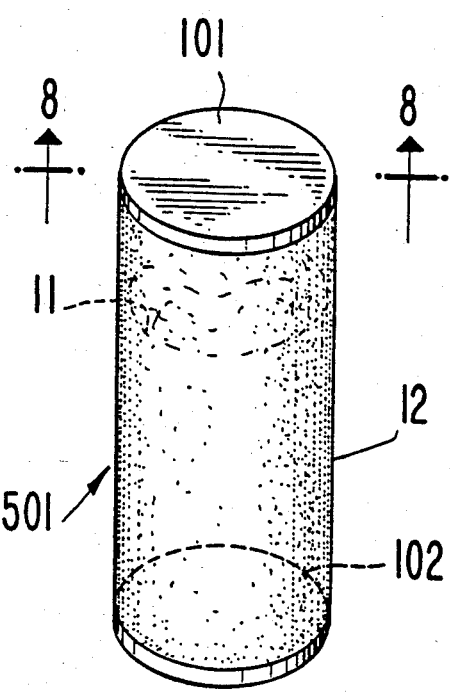
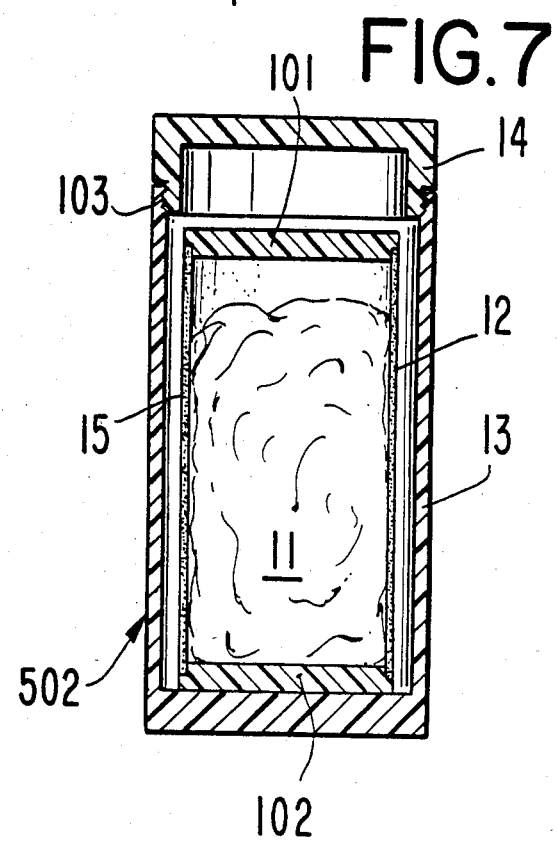
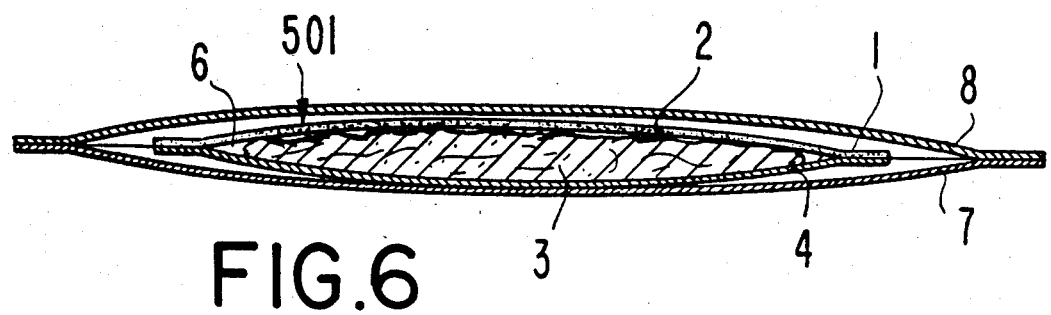

FIG. 22B
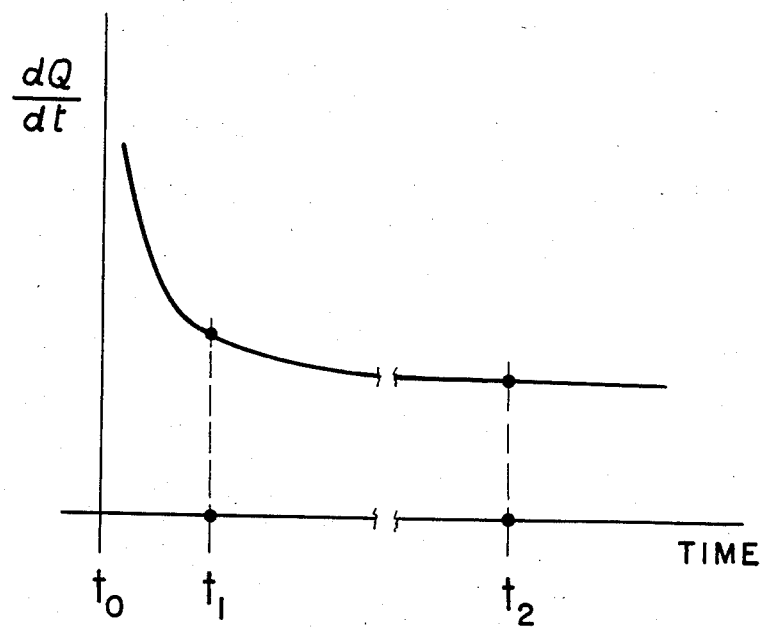
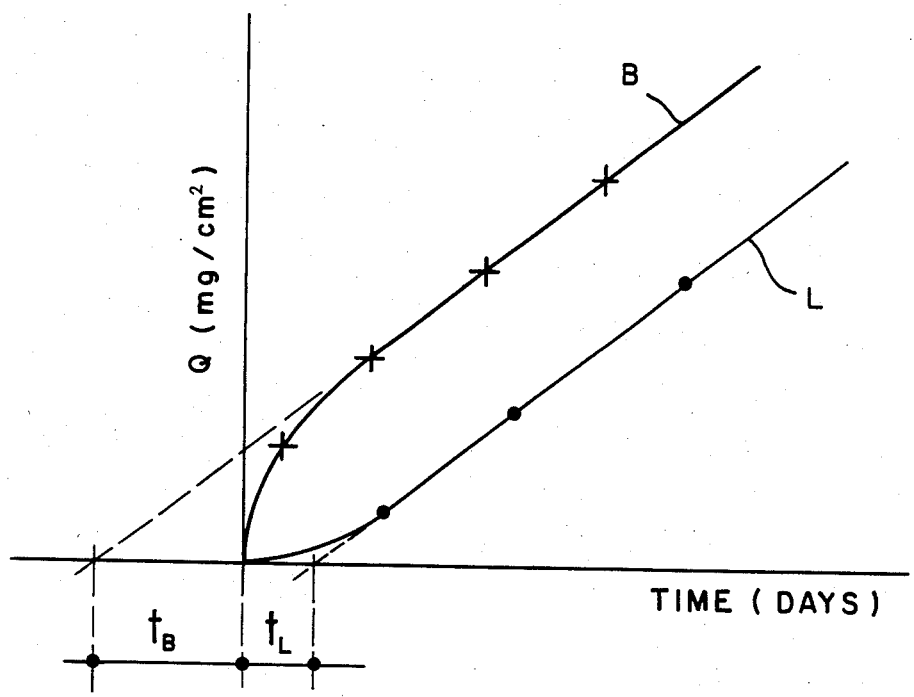
FIG. 22C

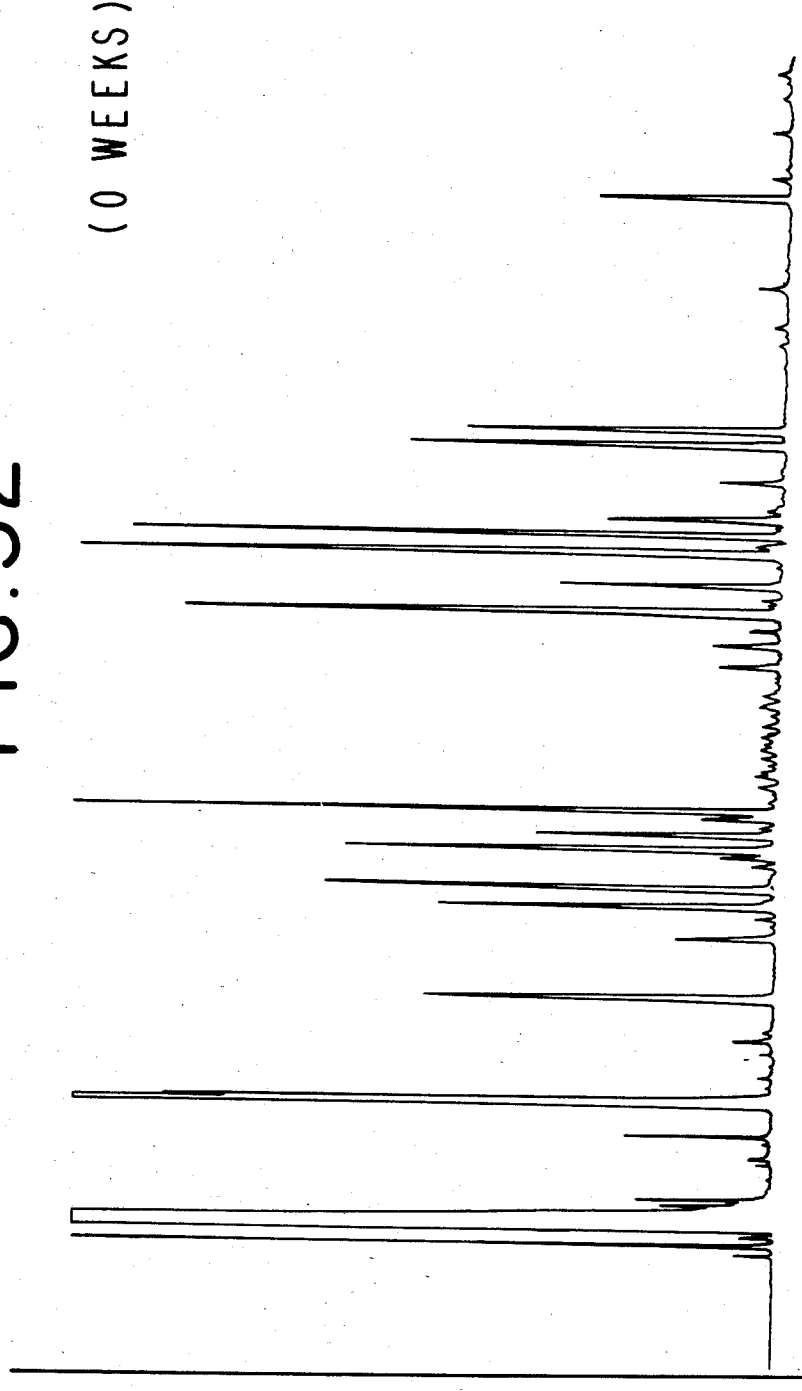

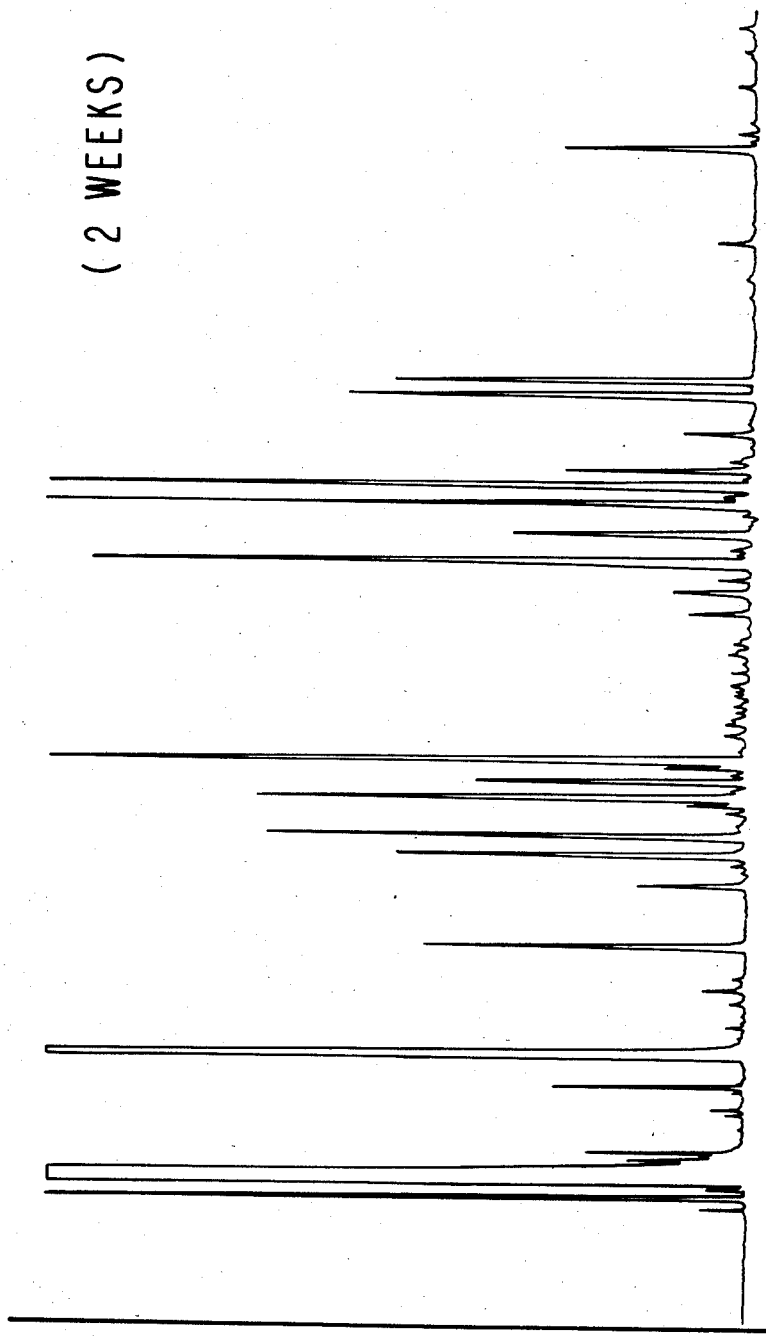
FIG.33 (2 WEEKS)
GLC PROFILE FOR EXAMPLE VI.

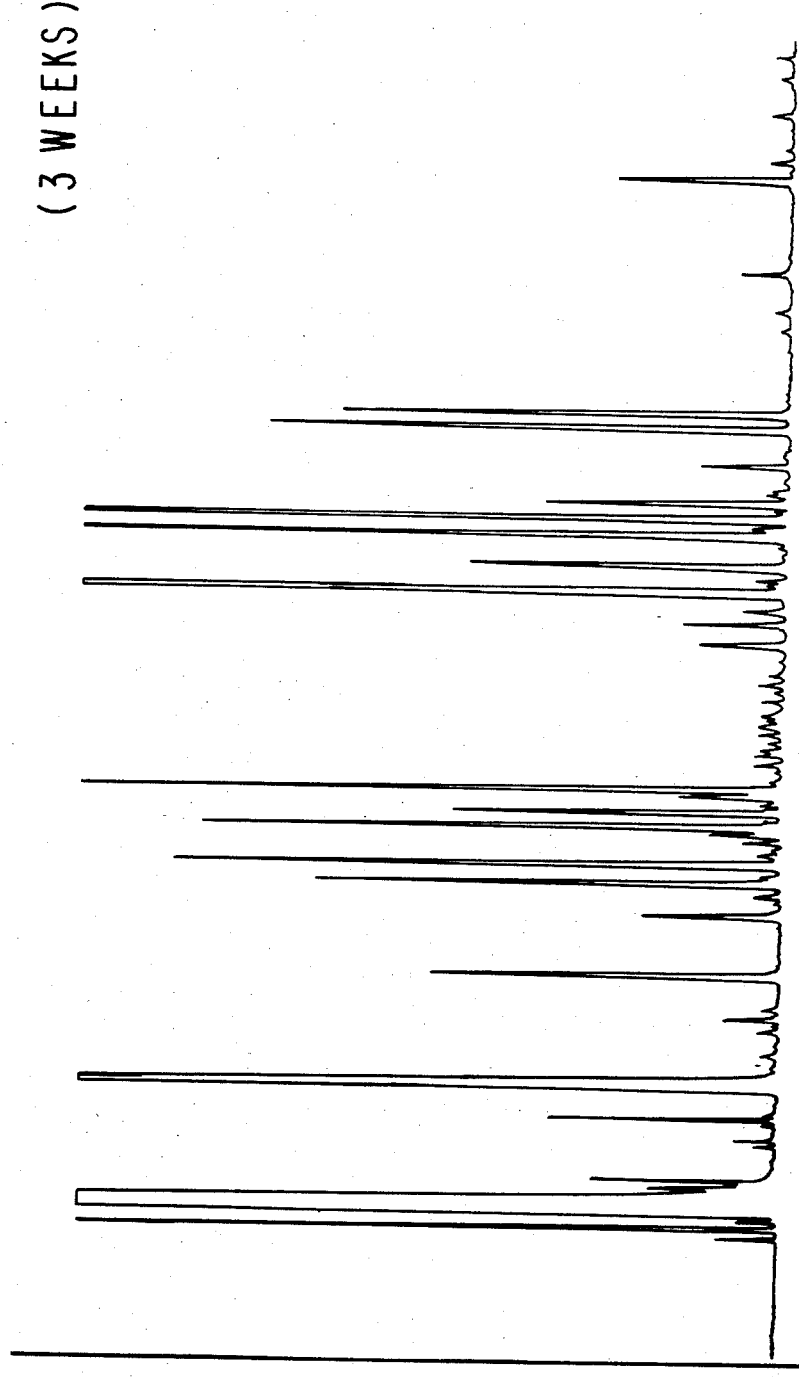
FIG. 34 (3 WEEKS)
GLC PROFILE FOR EXAMPLE VI.

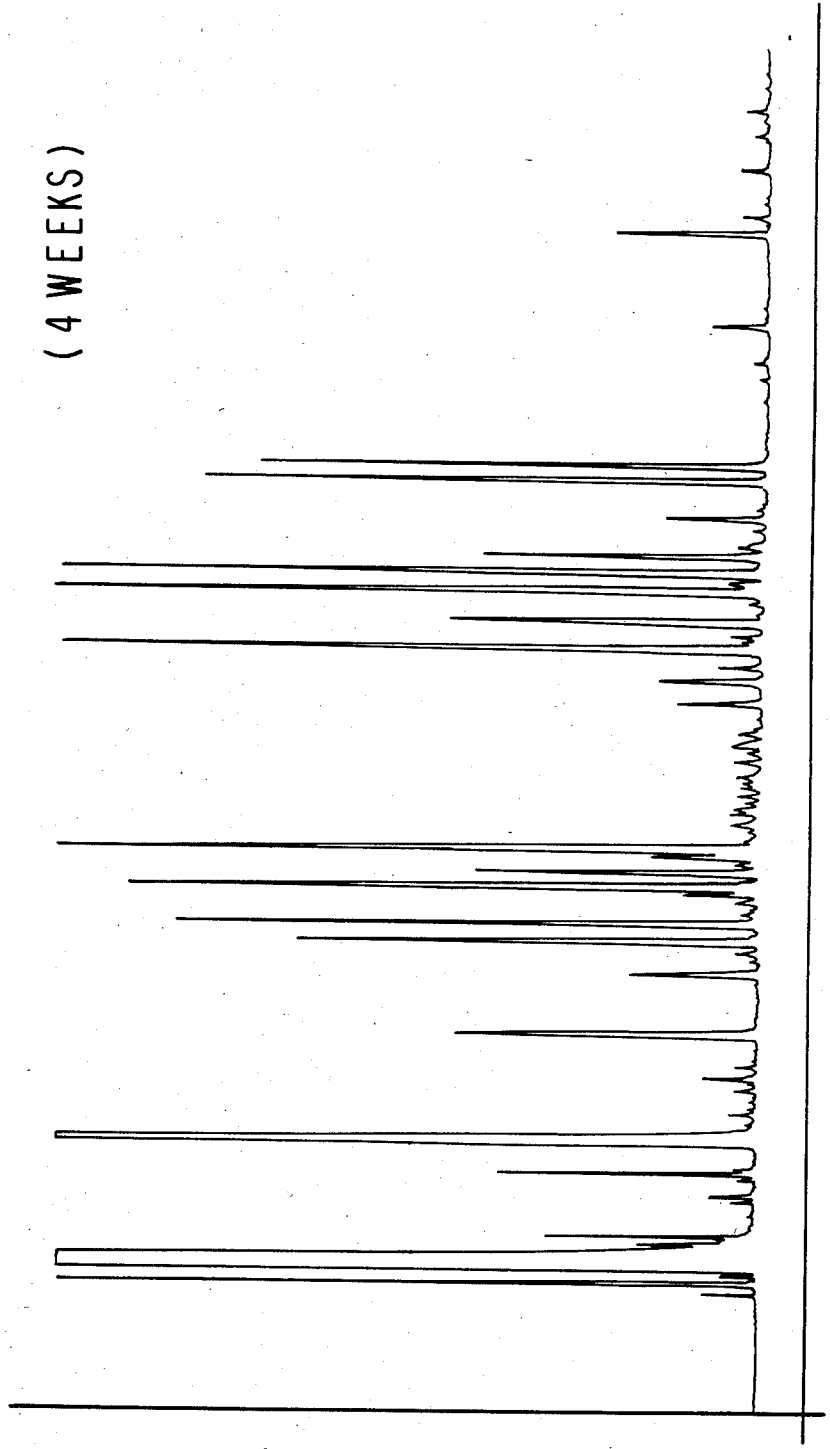
FIG. 35 (4 WEEKS)
GLC PROFILE FOR EXAMPLE VI.

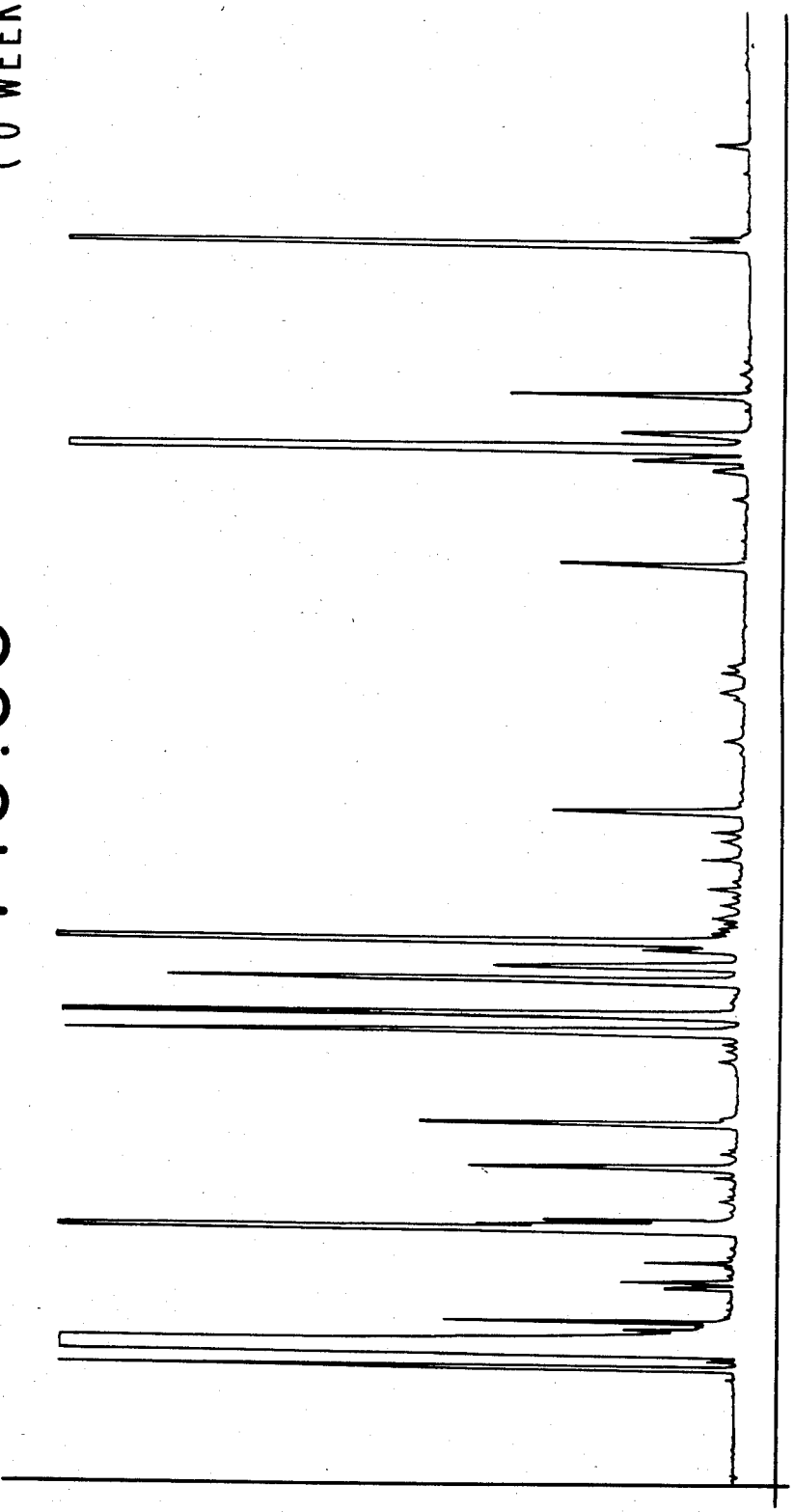

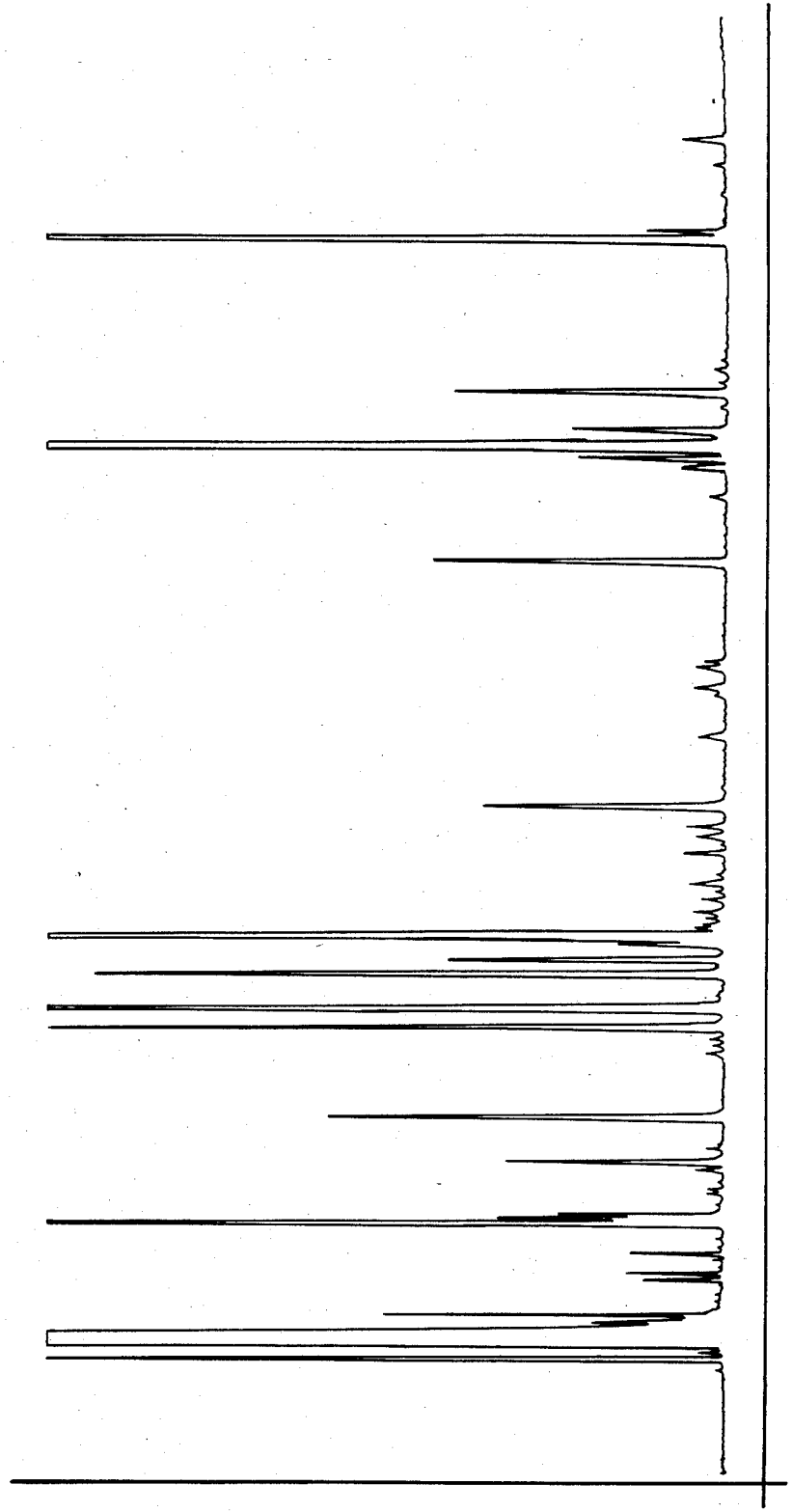
FIG.37 (2 WEEKS)
GLC PROFILE FOR EXAMPLE VI.

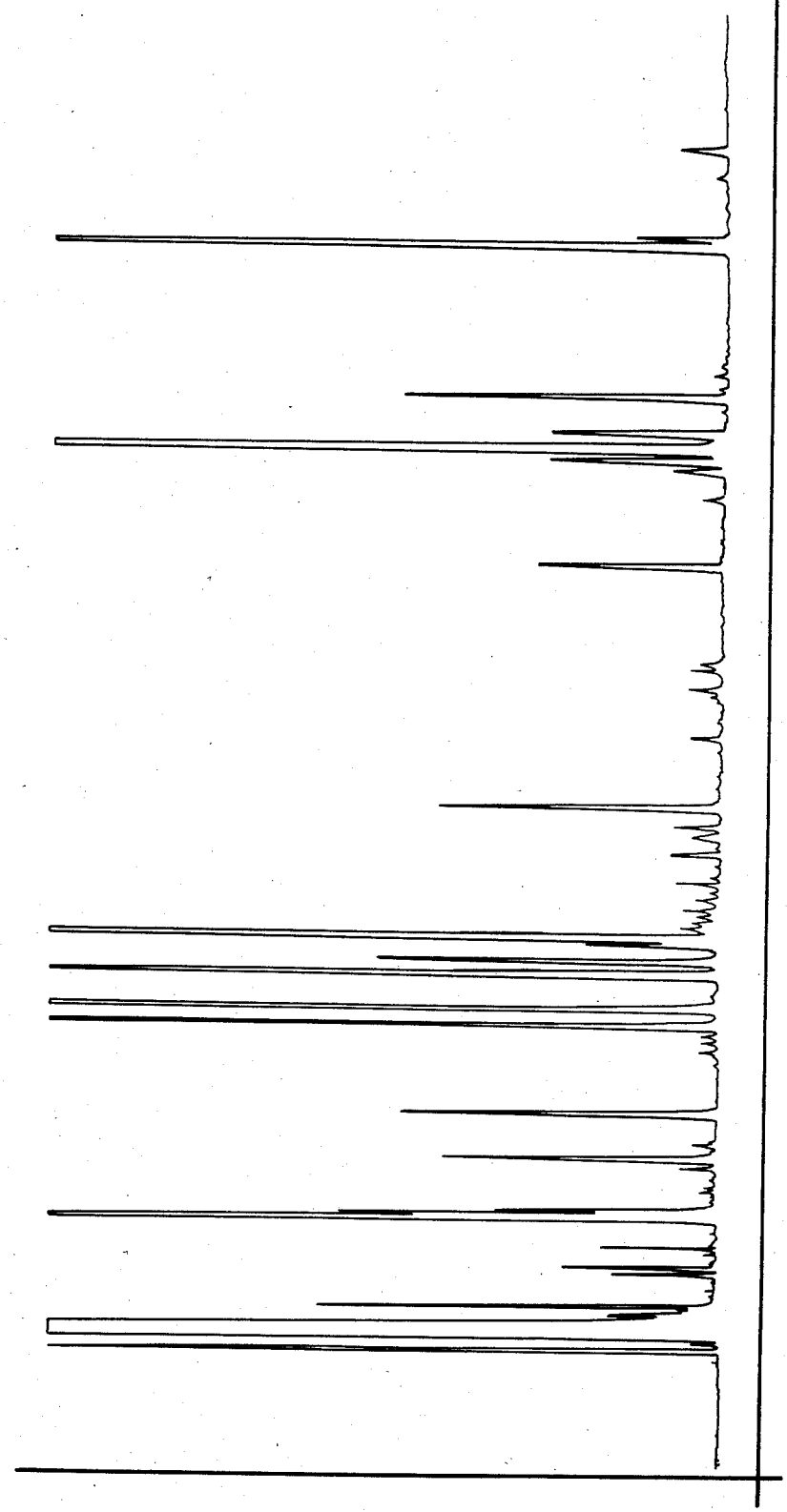

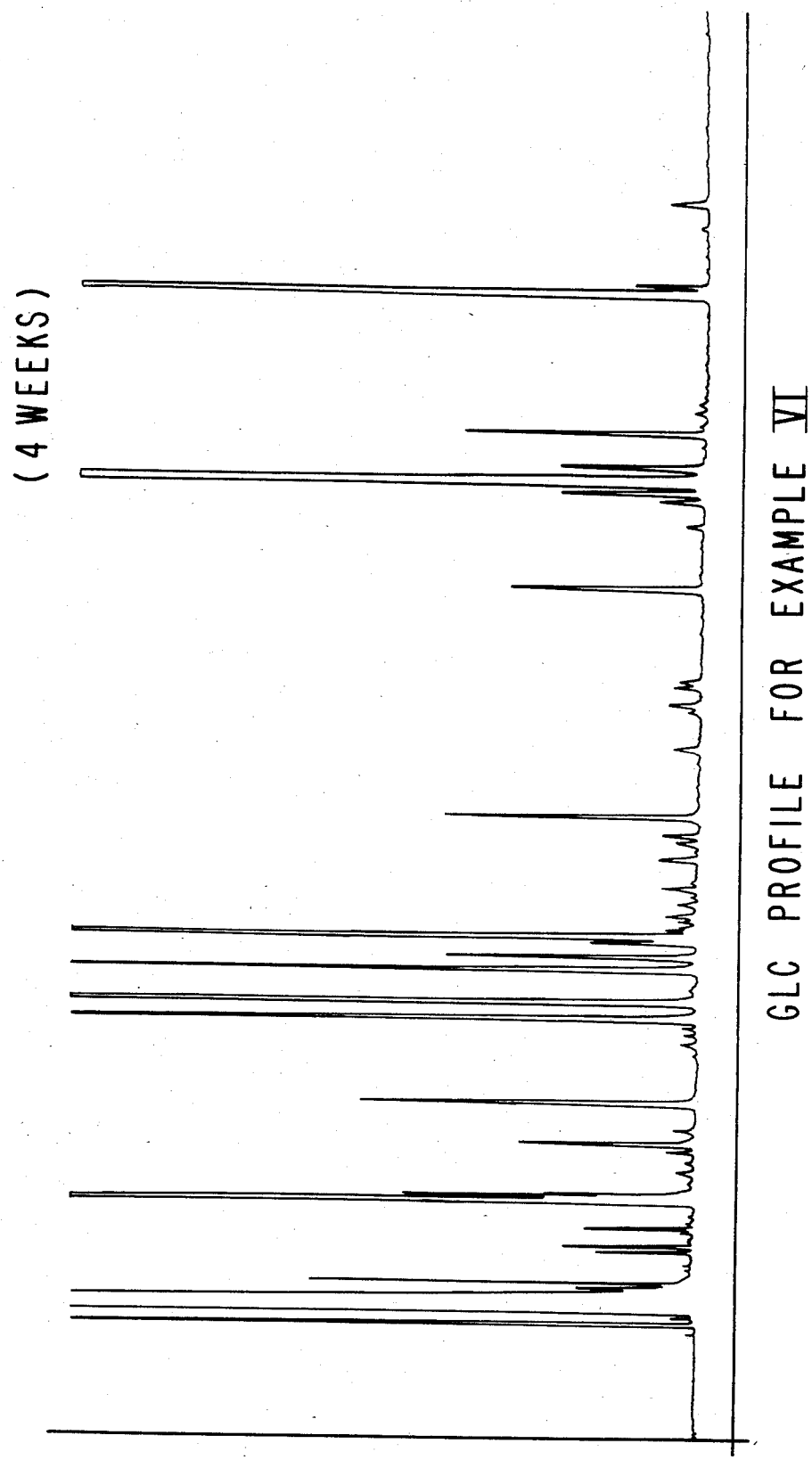
FIG.39 (4 WEEKS)
GLC PROFILE FOR EXAMPLE VI

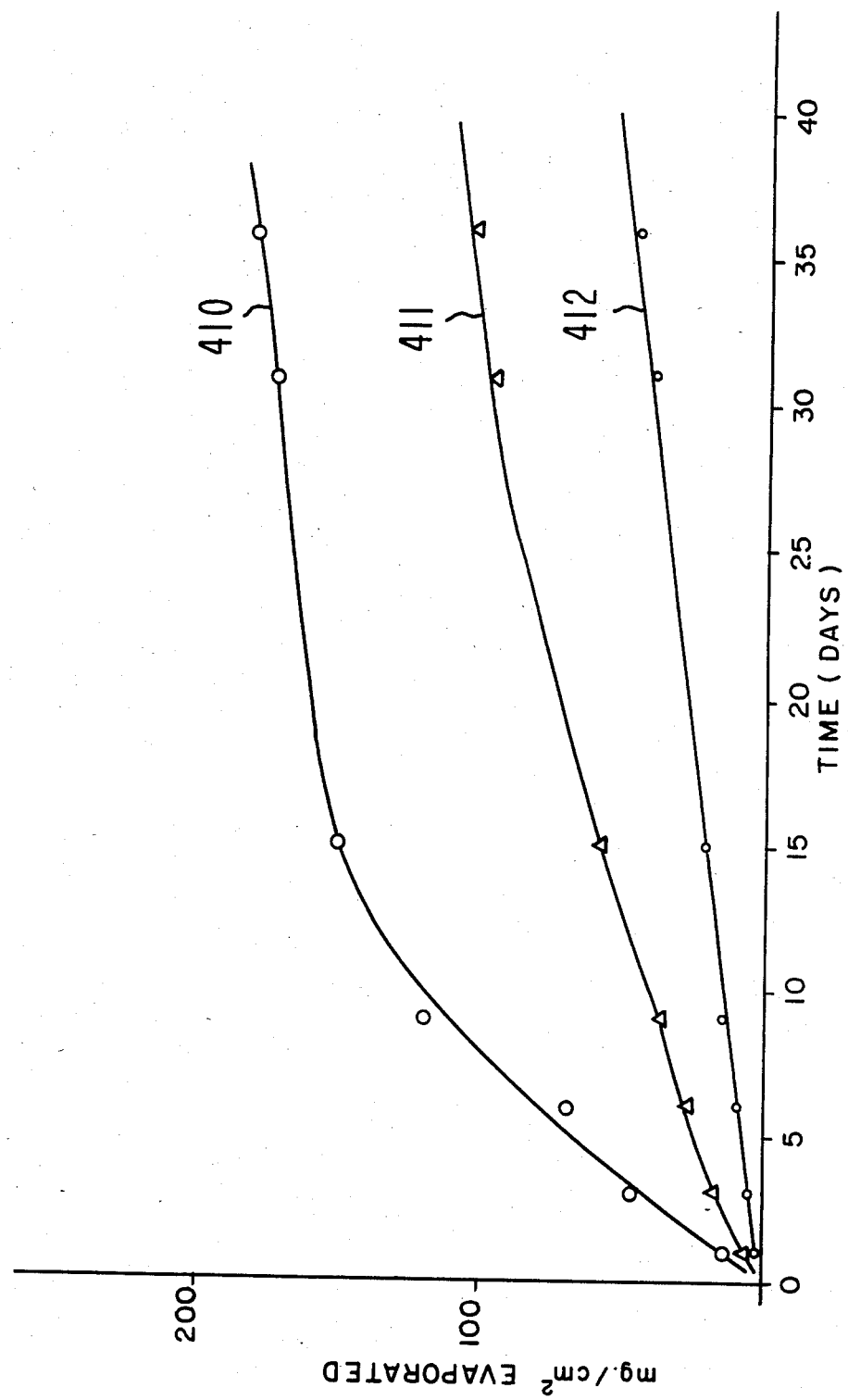

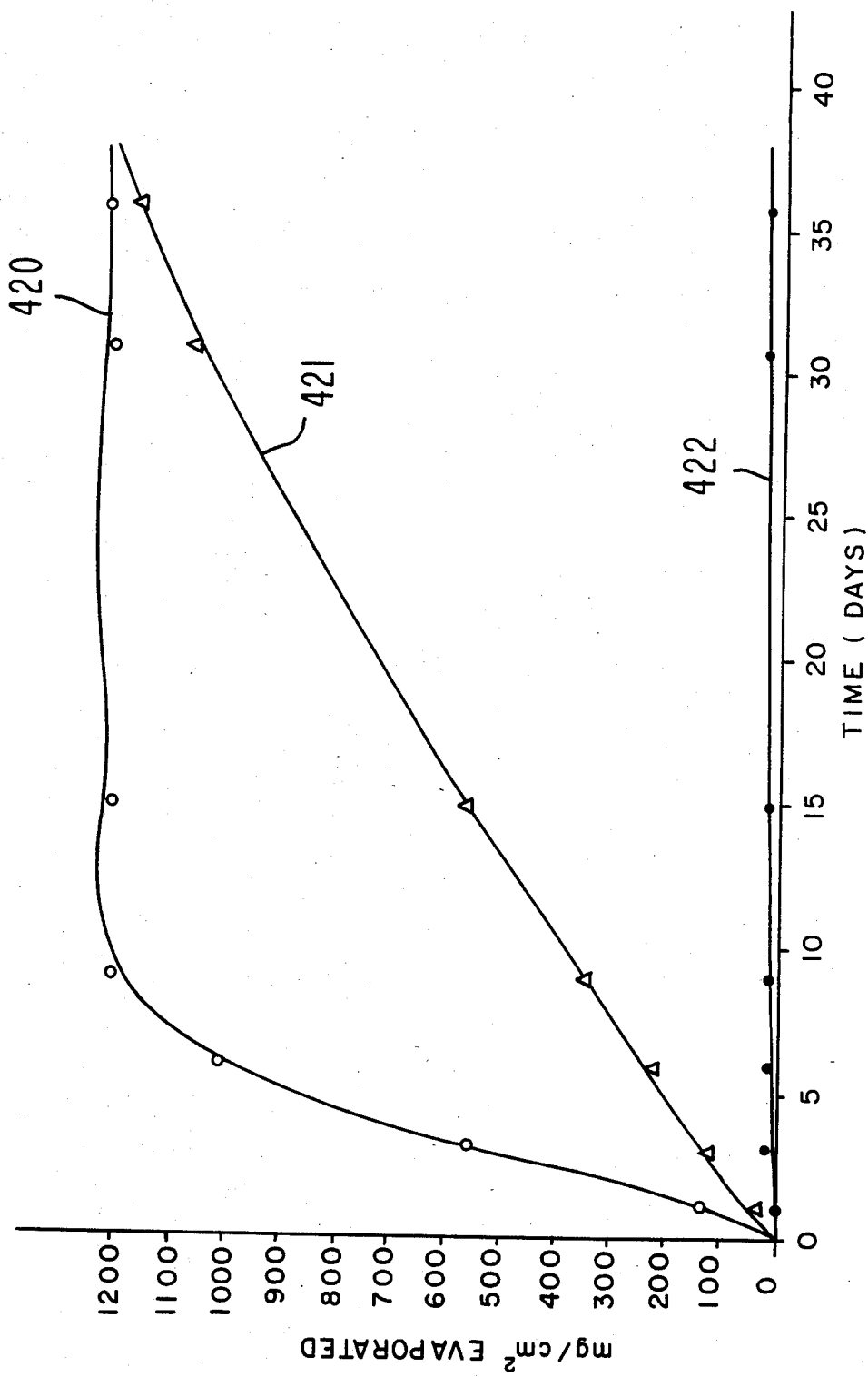

CONSTANT RATE VOLATILE COMPOSITION DISPENSING ARTICLE AND PROCESS FOR USING SAME

BACKGROUND OF THE INVENTION

As a result of using a polymer shell or film or sheet, monolayer, bilayer or multilayer, that is defined by having (i) the property of either transporting water vapor at a rate of between about 50 up to about 1000 g/m²/day at about 25° C. and at about 50% relative humidity at about atmospheric pressure and/or having an air transport rate of 100–20,000 Gurley seconds (Gs) and (ii) having a thickness in the range of from about 0.01 mils up to about 20 mils, our invention provides volatile substance-emitting apparatus and methods for producing same and for using same wherein the volatile substance can be an air freshener, a standard aromatizing material, an ordor maskant, an insecticide, an insect repellent, an animal repellent, compositions for evaluating olfactory functioning in humans, herbicides, pheromones and the like. These volatile substances have previously been used with the following delivery systems:
 aerosols;
 gels;
 paper;
 felt;
 large pore polymers;
 powders;
 candles; and
 wick-containing liquids.

With the exception of aerosols, the concentration and rate of release of volatile substance, e.g., perfume, into the atmosphere surrounding the container or emitting apparatus has been a function of the rate of evaporation of volatile material which, in turn, has been a function of the remaining concentration of volatile material in the container or emitting apparatus. This is the case in, for example, U.S. Pat. No. 4,161,283 issued July 17, 1979 Class 239 subclass 55 and U.S. Pat. No. 4,285,468 issued Aug. 25, 1981 Class 239 subclass 55. Accordingly, the rate of mass transfer (e.g., diffusion in certain instances) of the volatile substance into the surrounding atmosphere has, in the prior art, been "first order", that is, a function of the concentration previously present, e.g., for diffusion:

$$dc/dt = kc$$

where c is concentration of volatile material and k is a first order rate constant.

Furthermore, with respect to the apparatus of the prior art there has been no practical way for ascertainment by the user as to whether the bulk of the volatile material has been depleted at a particular point in time.

Thus, in Japanese Patent No. J80-0036,515 assigned to Akane Soji KK, printings from which fragrance is gradually emitted are indicated to be produced by a process comprising (1) preparing fragrance-emitting ink compositions by dispersing (a) fragrance-emitting bases prepared by mixing perfume solutions with thermoplastic resins at elevated temperatures to homogenize the mixture, followed by cooling the mixture to separate fine particles of gelled resin in which the perfume is occluded in (b) a solution of film-forming material and (2) printing the base material with this fragrance-emitting ink composition.

Scent-releasing polyurethane foams are shown to be prepared in German published Application No. 2,945,757 (assigned to the Tenneco Chemical, Inc.). In published Application No. 2,945,757, it is indicated that a polyurethane foam containing a particulate filler and perfume is prepared by first mixing the filler with the perfume and adding this mixture to a liquid polyol and finally mixing the thus-obtained composition with an organic polyisocyanate, water and a catalyst to produce the resulting foam. It is indicated that the resulting material is used as an air freshener, deodorant, perfume sachet and the like. It is further indicated that the foam releases the perfume at a limited and constant rate. The said published German Application corresponds to U.S. Pat. No. 4,226,944 issued on Oct. 7, 1980.

U.S. Pat. No. 4,247,498 issued on Jan. 27, 1981 discloses a method for preparing a homogeneous microporous cellular polymer structure which evolves perfumes, insect repellents, odor masking agents and the like at a slow and steady rate. The process of U.S. Pat. No. 4,247,498 comprises (i) heating a mixture of a polymer which may be an olefinic polymer, condensation polymer, oxidation polymer or a blend thereof and a "compatible liquid" to a temperature and for a time sufficient to form a homogeneous solution, (ii) forming at substantially the same time a plurality of liquid droplets of substantially the same size in a continuous liquid polymer phase by cooling the solution, (iii) continuing cooling to solidify the polymer, (iv) then at least partially displacing the "compatible liquid" with a perfume, an odor masking agent, an insect repellent or the like. It is indicated at column 15, line 30 of U.S. Pat. No. 4,247,498 that the disclosed system may be used to create a "thin film of about 1 mil or less up to a relatively thick block of thickness of about 2⅜ inches".

Japanese published Application No. J5-5081,655 assigned to Kureha Chemical Industries KK discloses a slow release air aromatizing composition which comprises an aqueous solution of water soluble high molecular weight substance of viscosity 500–30,000 cps such as polyvinyl acetate, carboxymethyl cellulose, sodium alginate, xanthan gum, etc. admixed with an oil soluble perfume or a water soluble perfume.

U.S. Pat. No. 4,145,001 describes a package having plural layers with the quantity of volatile substance such as a deodorizer sandwiched between the layers. The outer layers of the laminate in U.S. Pat. No. 4,145,001 are impermeable to the substance and its vapors, and thus prevent the escape of vapors as long as the package is sealed. Upon opening of the package of U.S. Pat. No. 4,145,001, delamination occurs at the interface between two selected layers such that the volatile substance is covered on one side only by a layer of material which is permeable to the vapors, thereby allowing controlled release of the vapors over a period of time. A process for production of such package is also disclosed in U.S. Pat. No. 4,145,001.

U.S. Pat. No. 4,161,283 issued on July 17, 1979 discloses an article for the slow release of volatilizable substances such as deodorizers, insecticides, repellents and the like, the article being formed from opposed outer and inner wall members joined along their peripheral portions to define a central reservoir portion for receiving and confining a volatilizable substance. The outer wall in U.S. Pat. No. 4,161,283 comprises a nonporous flexible polymeric sheet material which does not permit bulk flow but allows molecular diffusion therethrough. The inner wall member comprises an impermeable barrier layer. Another barrier layer is releasably bonded to the outer wall and prevents escape of volatilizable substance until its removal at the time of desired used. U.S. Pat. No. 4,285,468 issued on Aug. 25, 1981 discloses essentially the same subject matter as U.S. Pat. No. 4,161,283.

Nothing in the prior art, however, discloses the use of a polymeric membrane (shell, film or sheet, monolayer, bilayer or multilayer) as defined by having (i) the property of either transporting water vapor at a rate of between about 50 up to about 1000 g/m$^2$/day at about 25° C. and at about 50% relative humidity at about atmospheric pressure and/or having an air transport rate of 100-20,000 Gurley seconds (Gs) and (ii) a thickness in the range of from about 0.01 mils up to about 20 mils which gives rise to the structure of our invention which is a commercially viable structure capable of dispensing controllably at an approximately constant rate, continuously or discontinuously, for discrete periods of time, a volatile composition of matter such as a perfume, an air freshener, an air deodorant or the like.

OBJECTS OF THE INVENTION

It is an object of our invention to provide a process for dispensing at an approximately constant rate, controllably, continuously or discontinuously, for discrete and controllable periods of time, volatile compositions of matter from a container into the environment surrounding such container.

It is a further object of our invention to provide a process for dispensing at an approximately constant rate, continuously or discontinuously for discrete and controllable periods of time volatile compositions of matter from a container into the atmosphere surrounding such container enabled by the use of a polymer shell or film or sheet, monolayer, bilayer or multilayer that is defined by having (i) the property of either transporting water vapor at a rate of between about 50 up to about 1000 g/m$^2$/day at about 25° C. and at about 50% relative humidity at about atmospheric pressure and/or having an air transport rate of 100-20,000 Gurley seconds (Gs) and (ii) a thickness in the range of from about 0.01 mils up to about 20 mils.

It is a further object of our invention to provide an apparatus useful for performing the process for dispensing at an approximately constant rate, controllably, continuously or discontinuously for discrete periods of time, such volatile compositions of matte.

It is a further object of our invention to provide a process for dispensing, controllably, continuously or discontinuously, for discrete periods of time, a perfume or air freshener or other volatile substance from a container into the environment surrounding said container, so that when the effective volatile composition of matter is depleted, the fact of actual depletion as well as the rate of depletion is easily determinable.

SUMMARY OF THE INVENTION

Our invention utilizes a polymer shell or film or sheet, monolayer, bilayer or multilayer that is defined by having (i) the property of either transporting water vapor at a rate of between about 50 up to about 1000 g/m$^2$/day at about 25° C. and at about 50% relative humidity at about atmospheric pressure and/or having an air transport rate of 100-20,000 Gurley seconds (Gs) and (ii) a thickness in the range of from about 0.01 mils up to about 20 mils for enabling a process to take place for dispensing in a controllable manner, continuously or discontinuously for discrete periods of time at a substantially constant rate ovr an overall extended period of time a volatile composition of matter from a container into the environment surrounding the container. Our invention also provides apparatus necessary and useful for carrying out this process. The apparatus includes a hollow total enclosed structure comprising a thin shell totally enclosing an inner void, the thin shell having a base portion and an upper portion, said base porition having an inner surface:

(i) contained totally within the inner void of the thin shell, a volatile composition (which may optionally be temporarily entrapped in an entrapment material and totally entrapped in the entrapment material at least at the instant in time of commencement of the functional operation of the structure—that is, when it is removed from an air-tight package); and (ii) at least a finite section of said thin shell comprising a porous polymer that is defined by having (i) the property of either transporting water vapor at a rate of between about 50 up to about 1000 g/m$^2$/day at about 25° C. and at about 50% relative humidity at about atmospheric pressure and/or having an air transport rate of 100-20,000 Gurley seconds (Gs) and (ii) a thickness in the range of from about 0.1 mils up to about 20 mils, (e.g., a filled porous polymer containing imbedded therein a plurality of finite solid particles) said porous polymer having a porosity such that when said hollow totally enclosed structure is located in the ambient environment, said volatile materials are transported through the porous polymer at a substantially constant mass flow rate both of the individual volatile components and totally through said porous polymer shell section, the driving force of such molecular transport resulting from a difference in concentration of volatile substance between:

(x) the gas phase of the inner void of said shell; and
(y) the gas phase-containing space immediately adjacent the outer surface of said microporous polymer shell section.

Preferably, the microporous polymer shell section (also referred to herein as "limina") useful in the practice of our invention has the following specifications:

(i) The property of transporting water vapor at a rate of between about 50 up to about 1000 g/m$^2$/day at about 25° C. and at about 50% relative humidity at about atmospheric pressure;
(ii) Porosity range: 100-20,000 Gurley seconds;
(iii) Most preferred porosity range: 8,000-12,000 Gurley seconds;
(iv) Range of Temperature for Operation: −80° C. up to 150° C.;
(v) Most preferred temperature range of Operation: 0° C.-60° C.;
(vi) A thickness in the range of from about 0.01 mils up to about 20 mils.

Certain statements concerning operation of the microporous polymer film of our invention are based upon information disclosed in the paper: "PERMEATION OF PURE GASES UNDER PRESSURE THROUGH ASSYMETRIC POROUS MEMBRANES, MEMBRANE CHARACTERIZATION AND PREDITION OF PERFORMANCE", Rangarajan, et al, *Ind.Eng.Chem. Proc.Des.Dev.*, 1984, 23, 79–87 the disclosure of which is incorporated by reference herein.

The term "polymer" in this case is intended to include polymers of varying molecular weights and degrees of branching, homopolymers, copolymers, terpolymers and the like, including but not limited to substances such as polyolefins (e.g., polypropylene), polyamides (e.g., nylon 66), polyfluorocarbons (e.g., TEFLON ®), polyesters, e.g. polyethylene terephthalate, polycarbonates, e.g., LEXAN ®, polyacrylates, e.g., LUCITE ® and blends of same in various molar ratios.

The term "membrane" is intended herein to define porous polymeric shells, films or sheets, monolayer, bilayer or multilayer which on functional operation of the structure of our invention and thereafter will have the ability to have transported therethrough volatile substances useful in the practice of our invention.

BRIEF DESCRIPTION OF THE DRAWINGS

FIG. 4 is an elevation view of the structure of FIG. 1 shown in cross section with the volatile substance completely spent.

FIG. 5 is a perspective view of a second preferred embodiment of the structure in accordance with our invention with a hollow cylinder fully loaded immediately prior to functional use thereof.

FIG. 6 is an elevation view of the apparatus of FIG. 1 shown in cross section fully loaded with volatile substance immediately prior to functional use thereof, the structure being located within an outer larger air-tight structure, the apparatus containing the entrapped volatile substance not being in functional use.

FIG. 7 is an elevation view of the cylindrical apparatus of FIG. 5 shown in cross section, with the volatile substance being fully loaded in said structure of FIG. 5, the structure of FIG. 5 contained in a larger enclosing cylinder which is air-tight whereby the structure of FIG. 5 is not in functional use.

FIG. 21 indicates three separate use (followed by storage) periods for the structure of FIG. 6.

Figure 1:
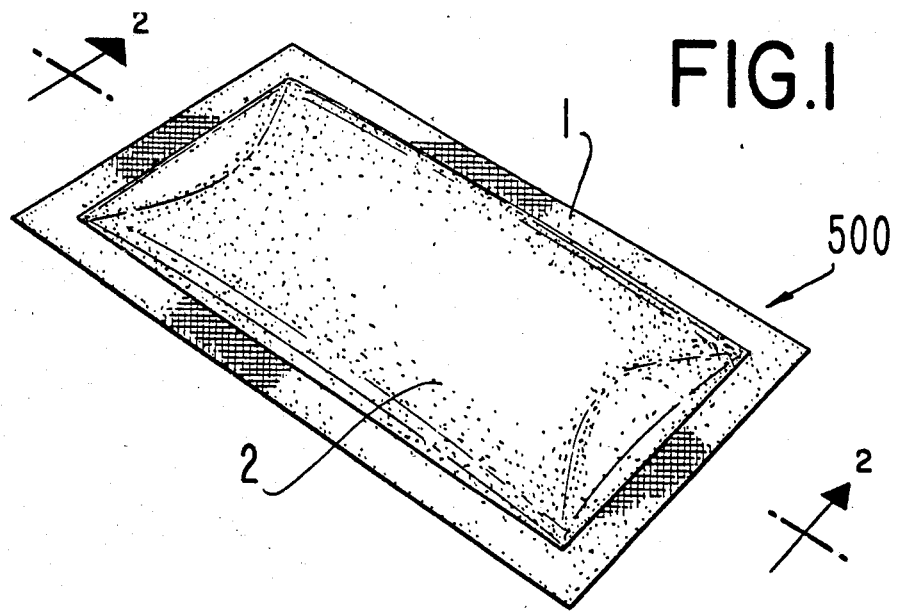
FIG. 1 is a perspective view of a preferred embodiment of the hollow totally enclosed structure of our invention, with the material of fabrication being flexible polypropylene film.
Figure 22:
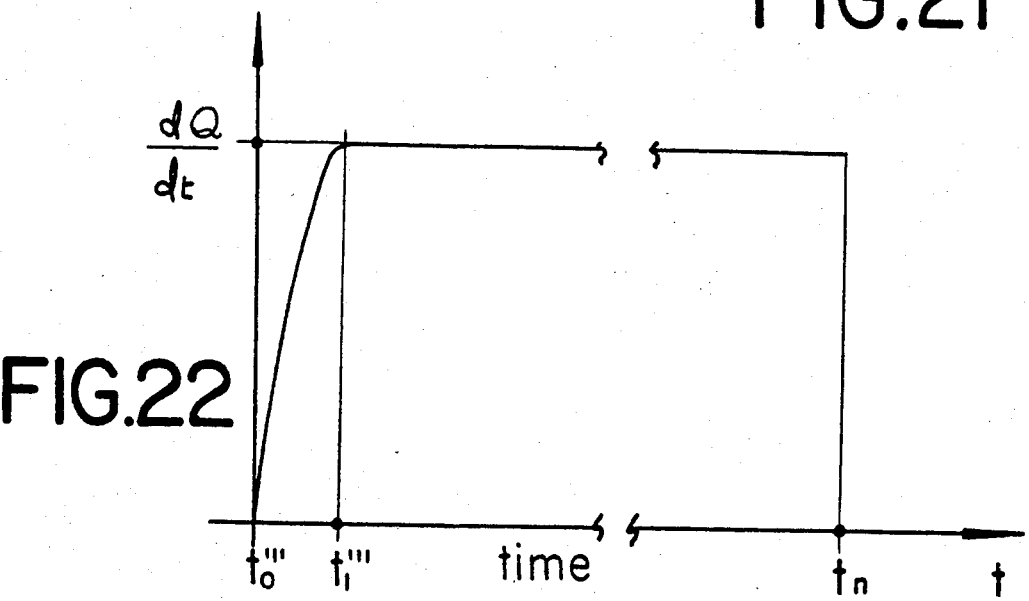
FIG. 22A represents a graph of rate of fragrance loss (dq/dt) versus time (resulting from a "time lag effect") for the entire period of possible continuous use of the structure FIG. 1 assuming that the structure of FIG. 1 is not replaced at discrete time intervals in an enclosed air-tight outer container.

FIG. 22B represents a graph of rate of fragrance loss (dq/dt) versus time (resulting from a "burst effect") for the entire period of possible continuous use of the structure of FIG. 1 assuming that the structure of FIG. 1 is not replaced at discrete time intervals in an enclosed air-tight outer container.

FIG. 22C represents graphs of fragrance loss versus time in the case of a "burst effect" (B) and in the case of a "lag effect" (L).

Figure 23:
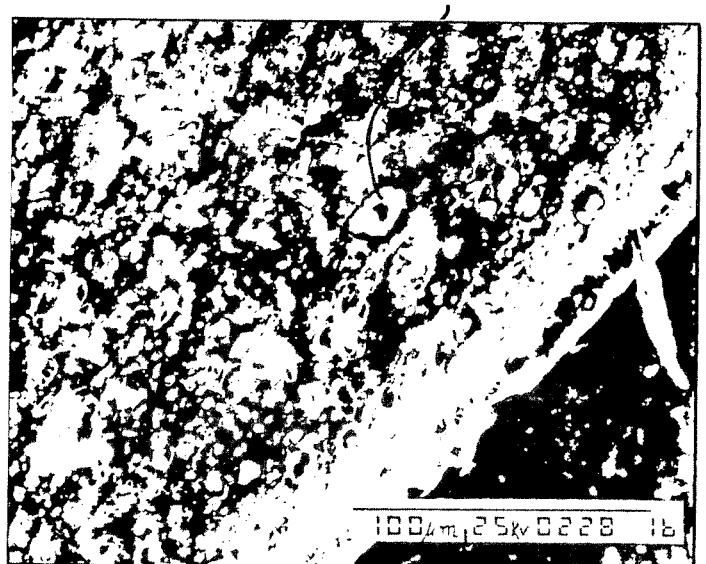

FIG. 23 represents a random section of a filled porous polymer lamina (12,000 Gurley second film) magnification of 500×, using a scanning electron microscope, which filled porous polymer lamina is useful in the practice of our invention.

Figure 24:

FIG. 24 represents a random section of a filled porous polymer lamina, (12,000 Gurley second film), magnification of 3500×, using a scanning electron microscope, which filled porous polymer lamina is useful in the practice of our invention.

Figure 25:
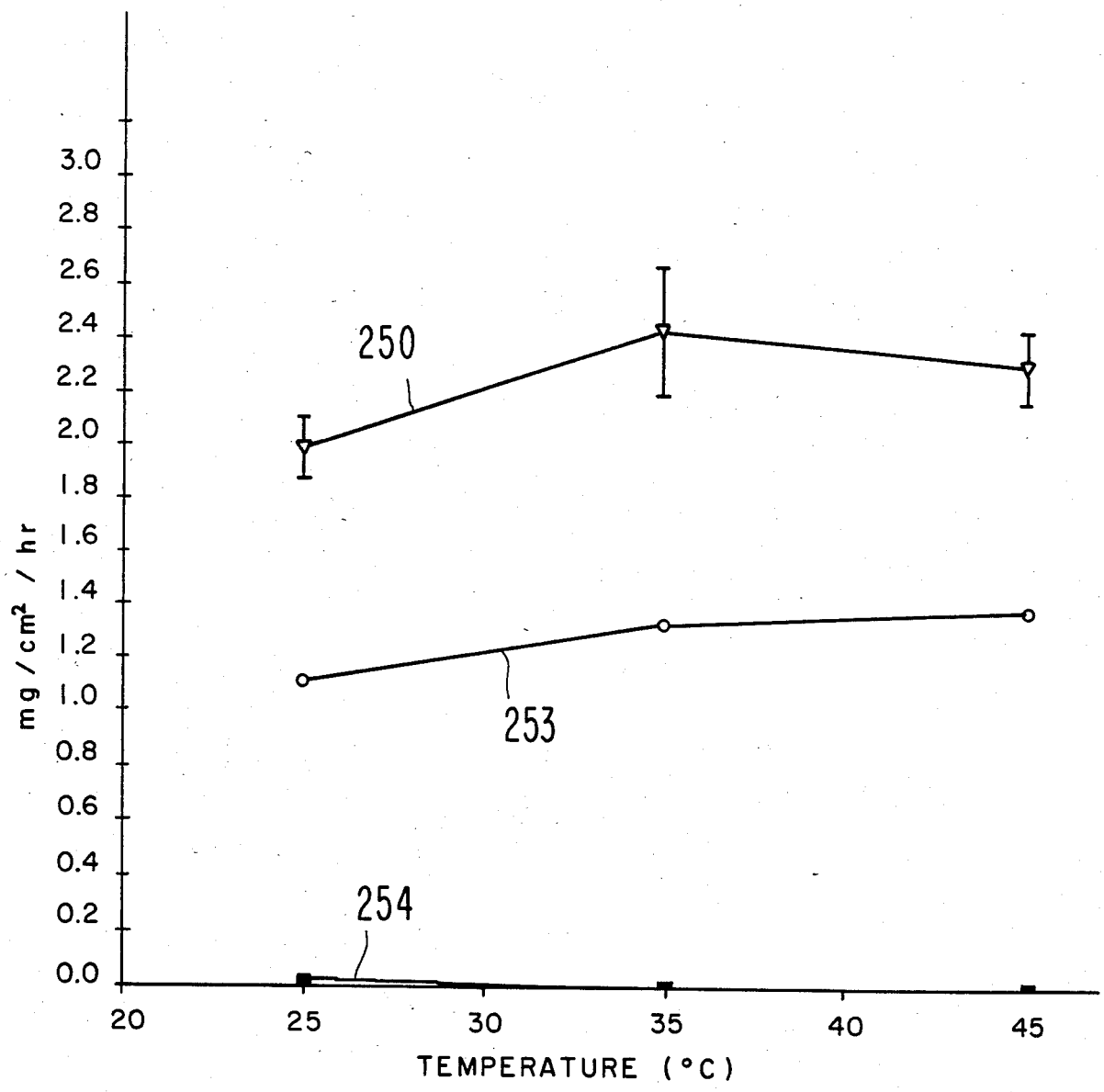

FIG. 25 is a plot of transport rate (of water vapor) versus temperature through filled porous polypropylene films of the nature exemplified herein, infra.

Figure 26:
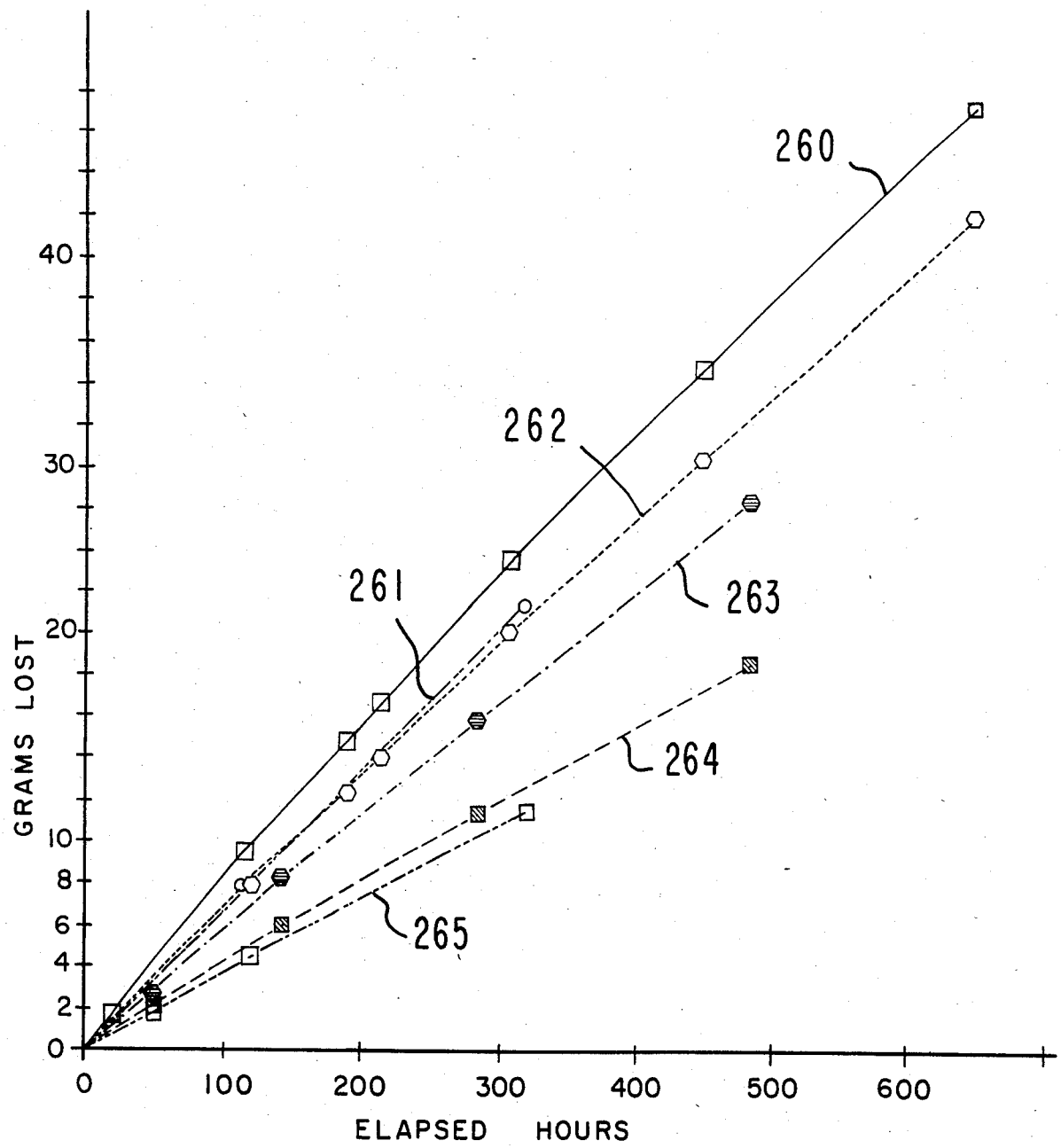
Figure 26:
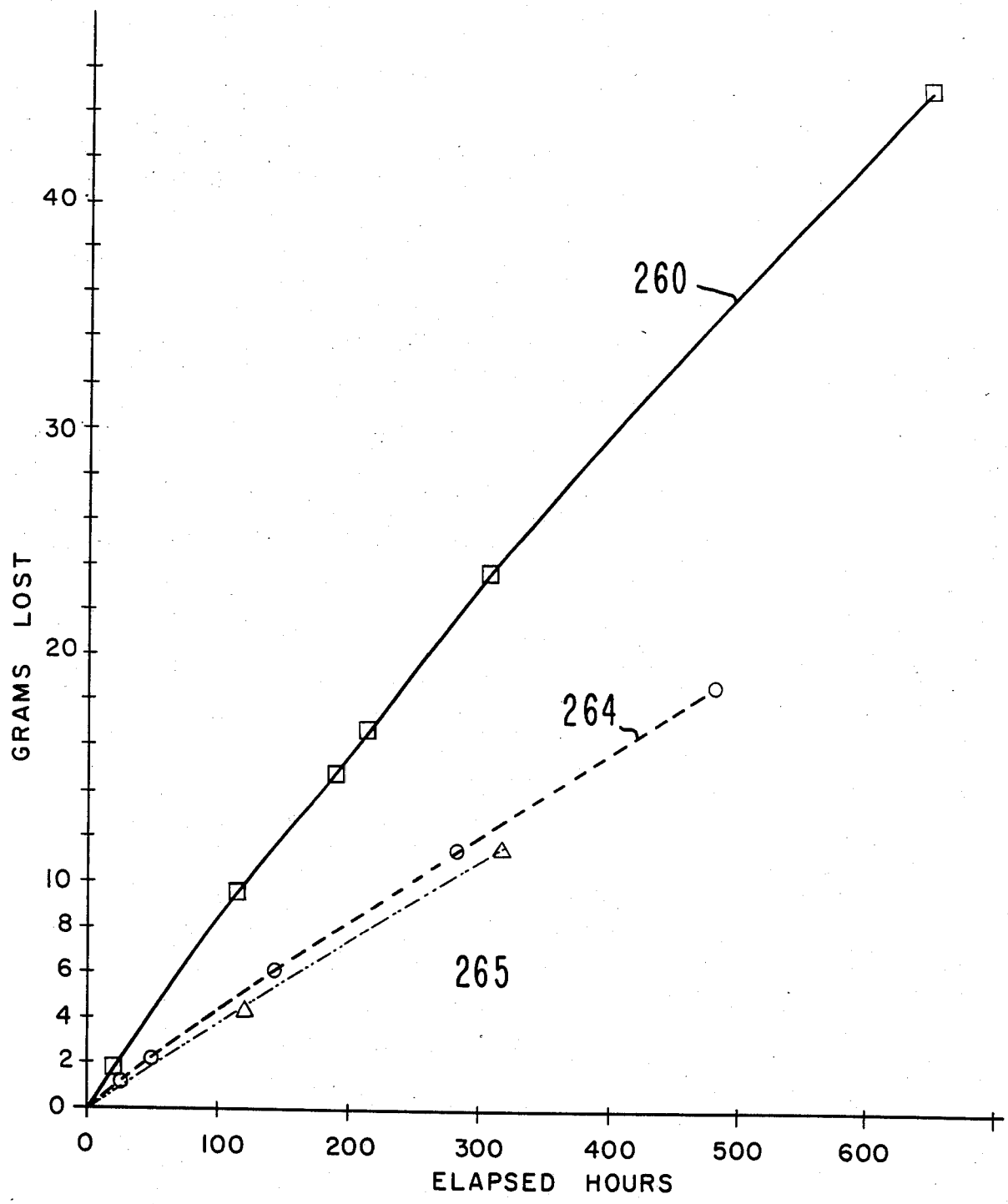

FIG. 26A is a series of graphs of time (elapsed hours) vs. grams water and fragrance lost from the article illustrated in FIG. 5 using various temperatures of operation. The data points are set forth in Example V, infra.

FIG. 26B is also a series of graphs of time (elapsed hours) vs. grams water and fragrance lost from the article illustrated in FIG. 5 using various temperatures of operation and working specifically with a fragrance identified as "278m". The method of obtaining such data is further specified in Example V, infra.

Figure 26C:
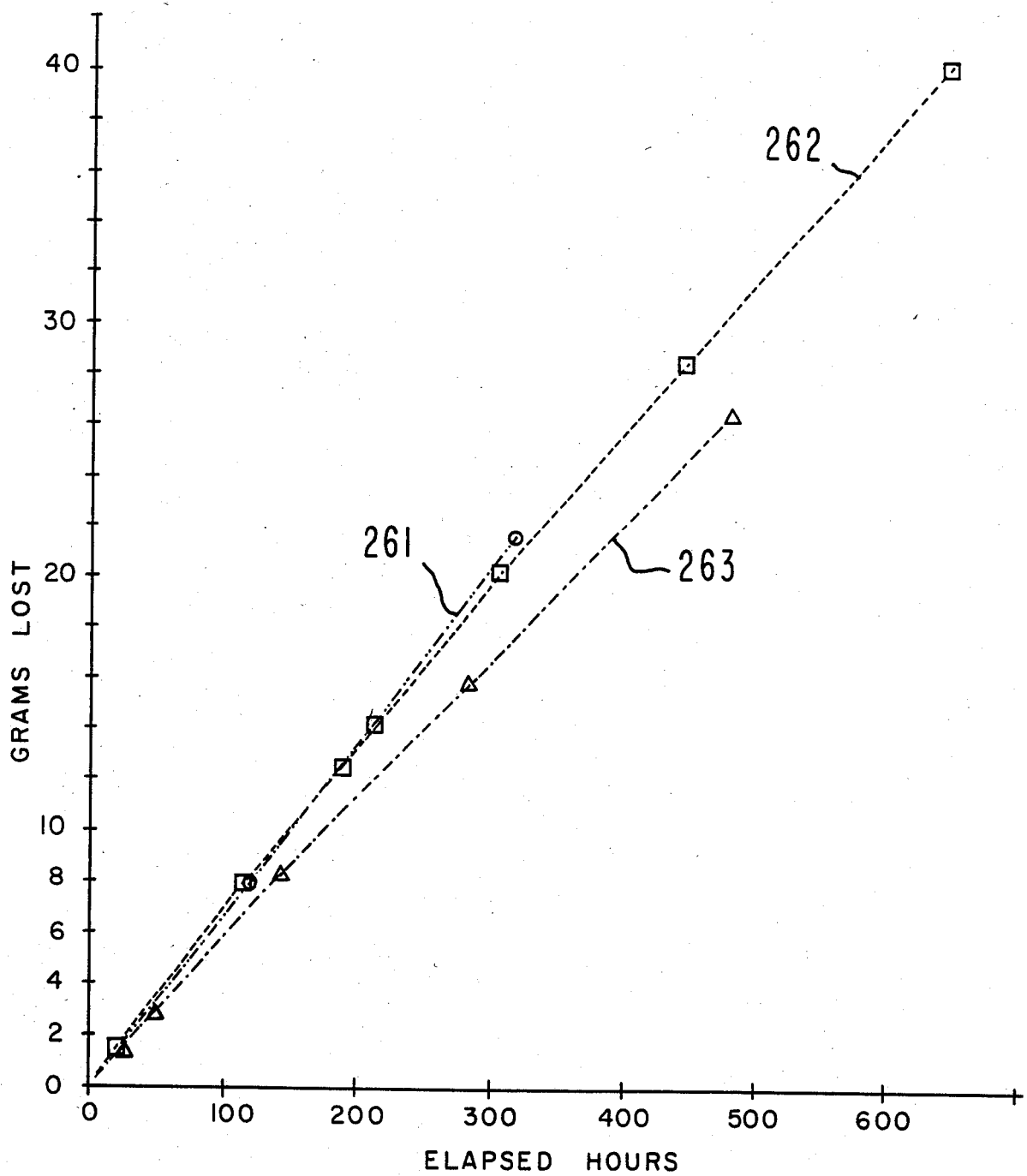

FIG. 26C is a series of graphs of time (elapsed hours) vs. grams water and fragrance lost from the article illustrated in FIG. 5 using various temperatures of operation and particularly working with a fragrance indicated as "894m" in Example V, infra.

Figure 27A:
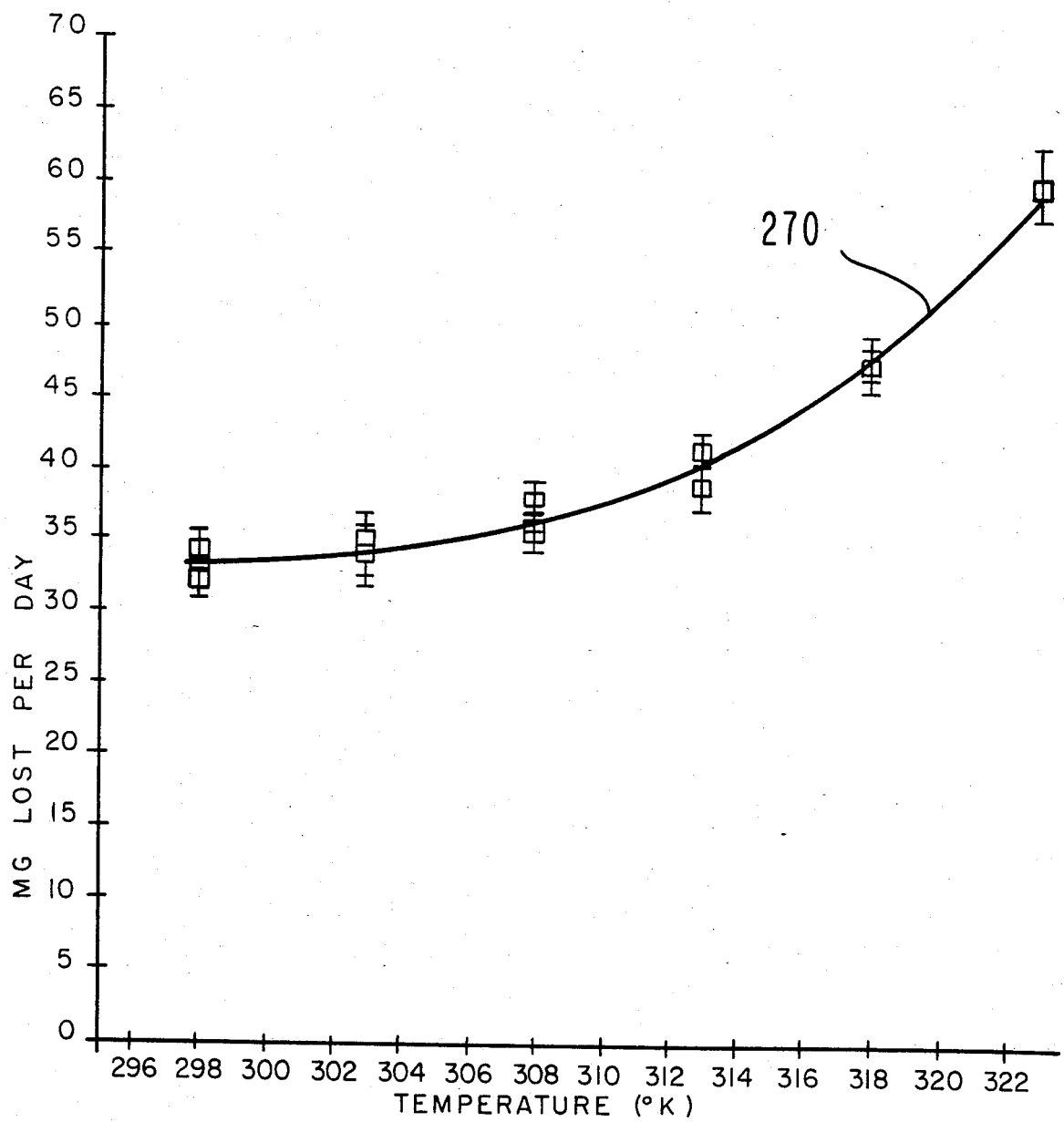

FIG. 27A sets forth a graph showing water transport through filled microporous polymeric membranes useful in the practice of our invention; and this graph sets forth mg water lost per day vs. temperature in degrees Kelvin.

Figure 27B:
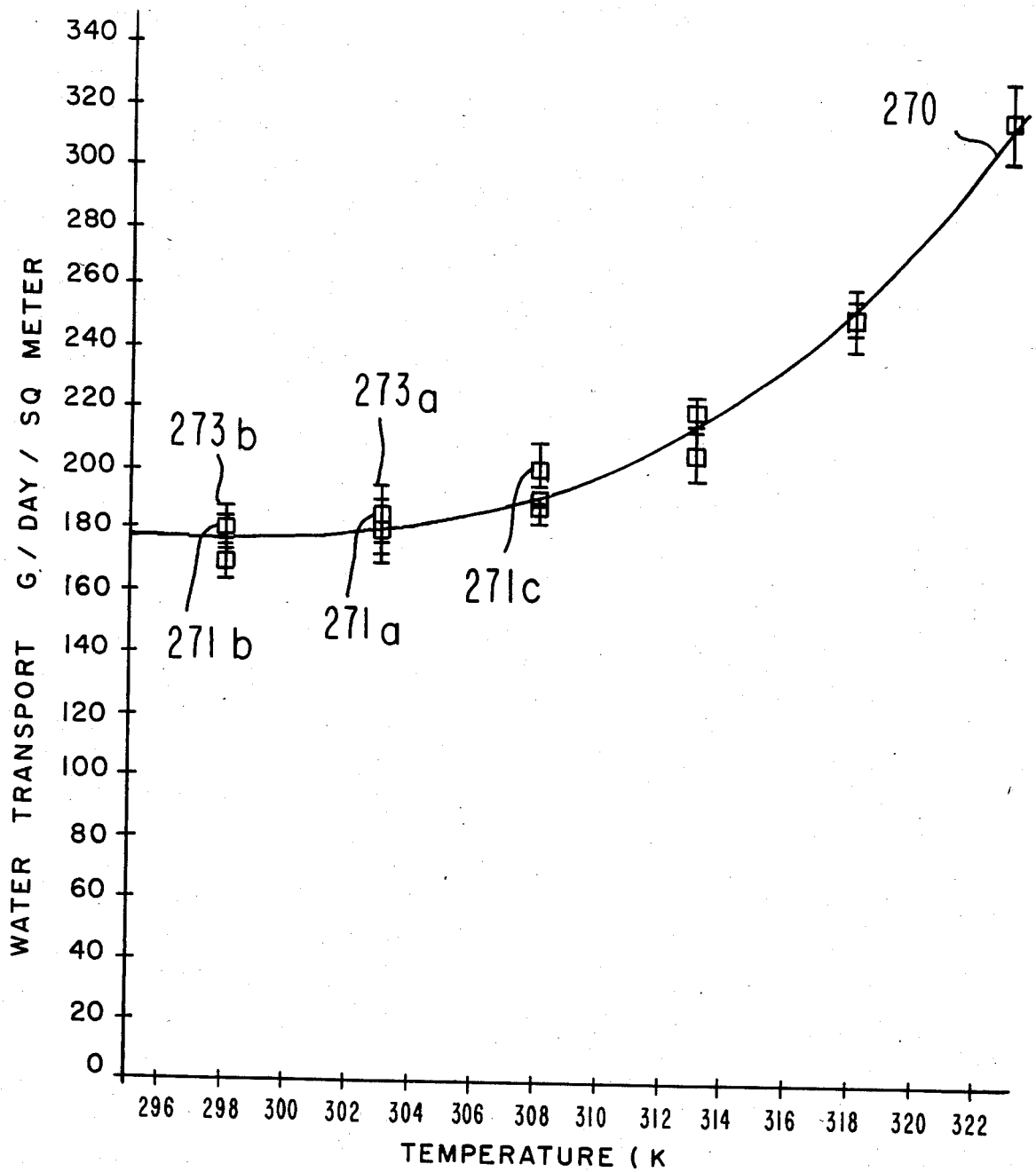

FIG. 27B sets forth a graph showing water transport through filled microporous polymeric membranes useful in the practice of our invention; and this graph sets forth grams water lost per day per square meter vs. temperature in degrees Kelvin.

Figure 28:
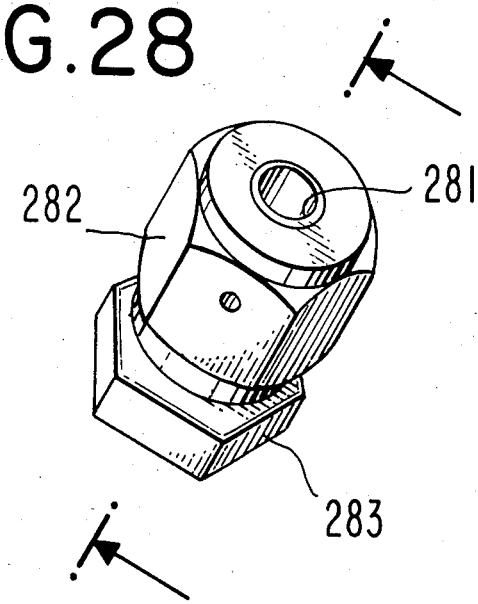

FIG. 28 is a perspective view of a cell used for determining the data as presented in the graphs of FIGS. 25, 26A, 26B, 26C, 27A and 27B.

Figure 29:
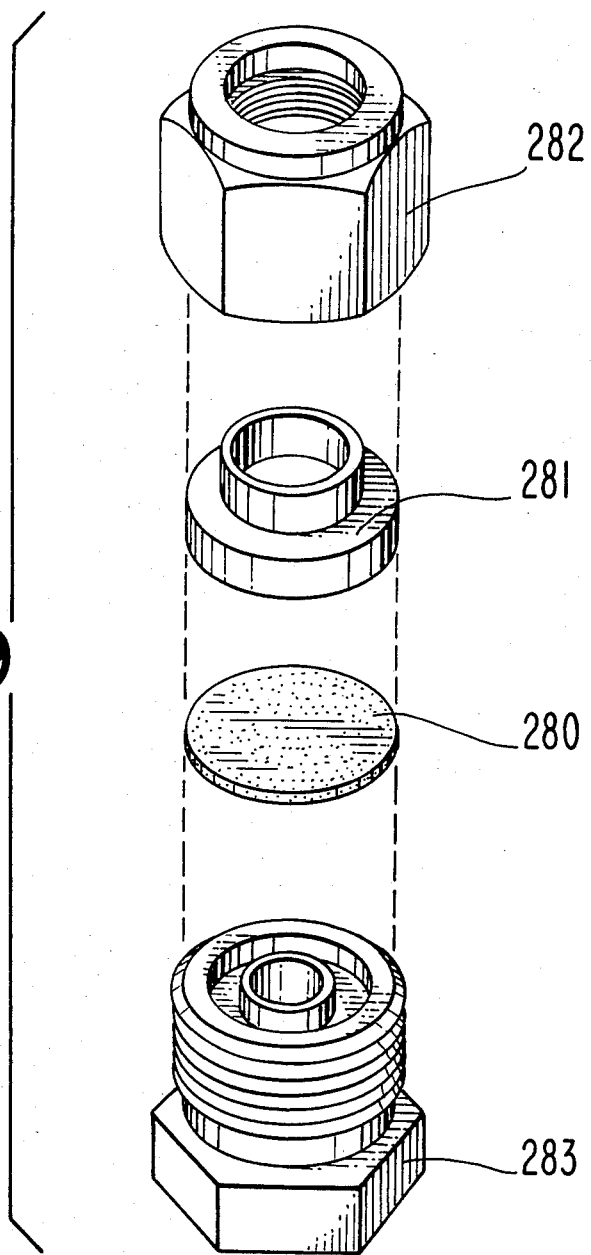

FIG. 29 represents an "explosion" of the parts of the cell of FIG. 28 and is indicative of how these parts are put together in order to enable the cell to be used to determine the data presented in the graphs of FIGS. 25, 26A, 26B, 26C, 27A and 27B, inclusive.

Figure 30:
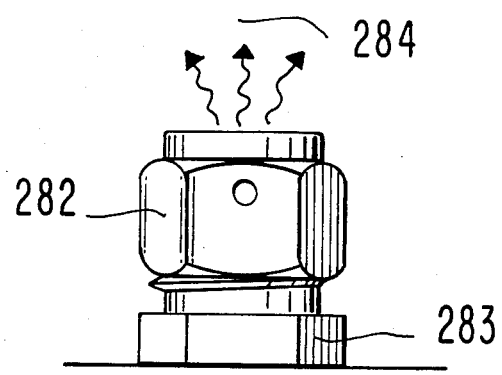

FIG. 30 is a side elevation view of the cell of FIG. 28.

Figure 31:
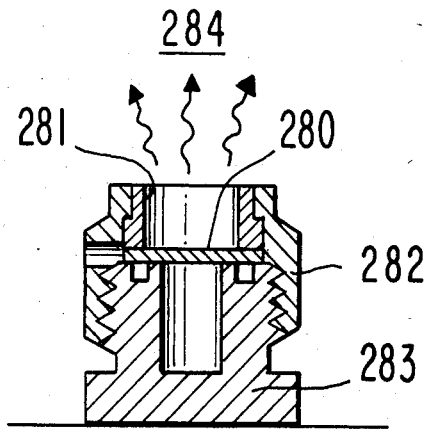

FIG. 31 is a cut-away side elevation view of the cell of FIG. 28 looking in the direction of the arrows.

FIG. 32 is a GLC profile of the fragrance material, denoted as "278m" employed in Example VI at time (t)=0 weeks.

FIG. 33 is the GLC profile for perfume composition "278m" employed in Example VI at (t)=2 weeks.

FIG. 34 is the GLC profile for perfume composition "278m" employed in Example VI at (t)=3 weeks.

FIG. 35 is the GLC profile for perfume composition "278m" employed in Example VI at (t)=4 weeks.

FIG. 36 is the GLC profile for perfume composition "894m" employed in Example VI at (t)=0 weeks.

FIG. 37 is the GLC profile for perfume composition "894m" employed in Example VI at (t)=2 weeks.

FIG. 38 is the GLC profile for perfume composition "894m" employed in Example VI at (t)=3 weeks.

FIG. 39 is the GLC profile for perfume composition "894m" employed in Example VI at (t)=4 weeks.

Figure 40:
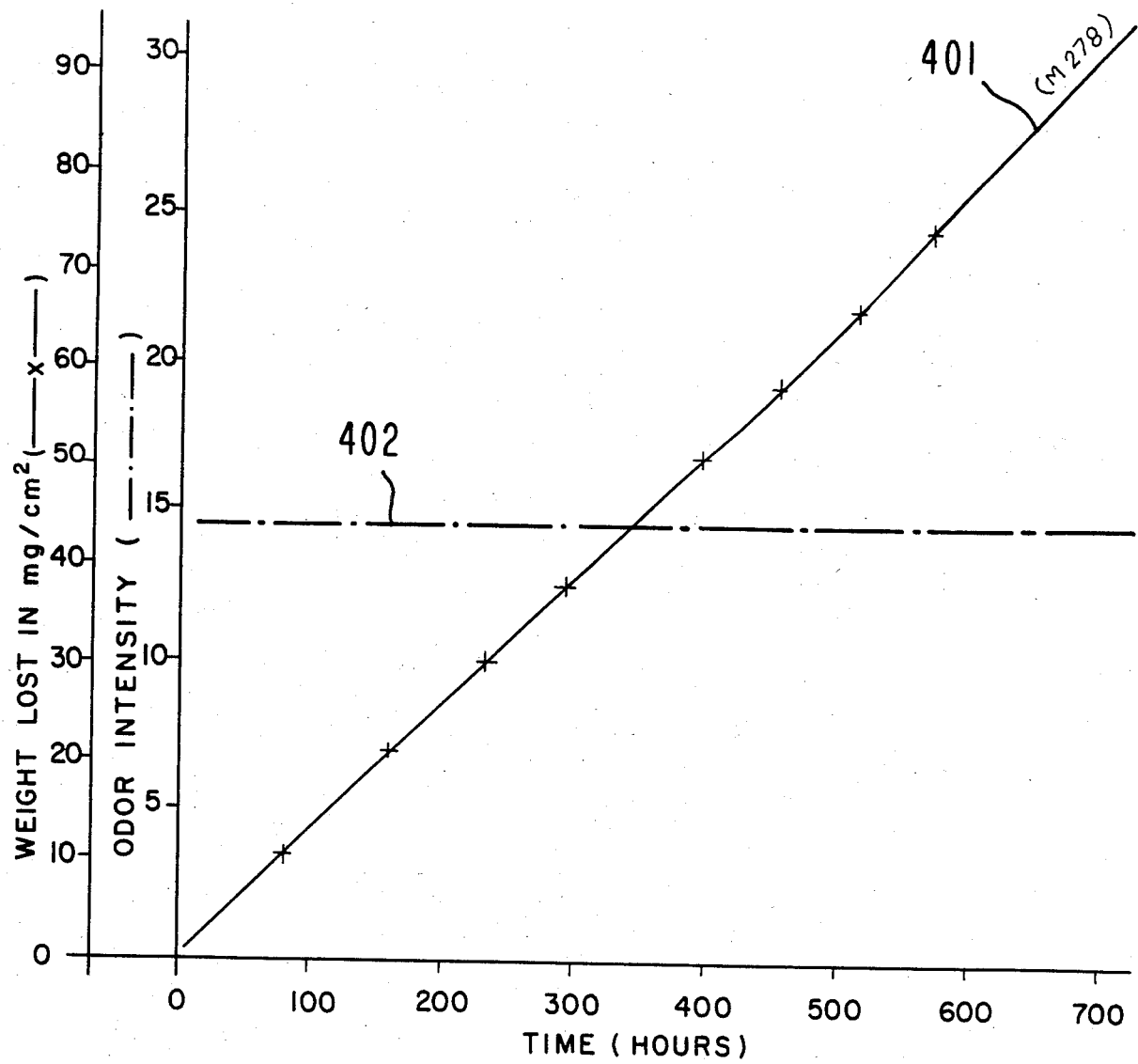

FIG. 40 is a dual graph for perfume composition "278m"; the graph indicated by reference numeral "401" showing weight loss over a period of time as measured in mg/cm$^2$ and the line indicated by reference numeral "402" indicating odor intensity vs. time (showing no change in odor intensity).

FIG. 41 represents a series of graphs indicating mg/cm$^2$ evaporated of fragrance through the membranes; a filled polypropylene membrane (reference numeral "411") and a non-filled polypropylene membrane (reference numeral "412"), and in addition, shows evaporation without the use of any membrane (reference numeral "410") as specifically set forth in detail in Example III, infra wherein the data points are set forth in tabular form.

FIG. 42 is another series of graphs showing evaporation in mg/cm$^2$ vs. time in days for a fragrance which is a 2% mixture of fragrance in Carbopol gel as specifically exemplified in Example III. The graph indicated by reference numeral "420" is a graph for evaporation without any interference from a membrane. The graph indicated by reference numeral "421" is the graph showing rate of evaporation through a membrane which is filled polypropylene and is a membrane defined according to our invention. The graph indicated by reference numeral "422" is the graph for evaporation through a polypropylene membrane, not defined within the parameters of our invention.

DETAILED DESCRIPTION OF THE INVENTION

Figure 2:
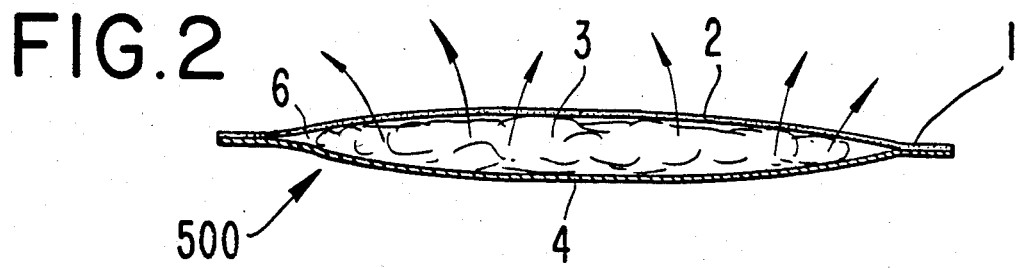
FIG. 2 is a cutaway elevation view of the hollow totally enclosed structure of FIG. 1 shown in cross section with the structure fully loaded with temporarily-entrapped volatile substance.
Figure 20:
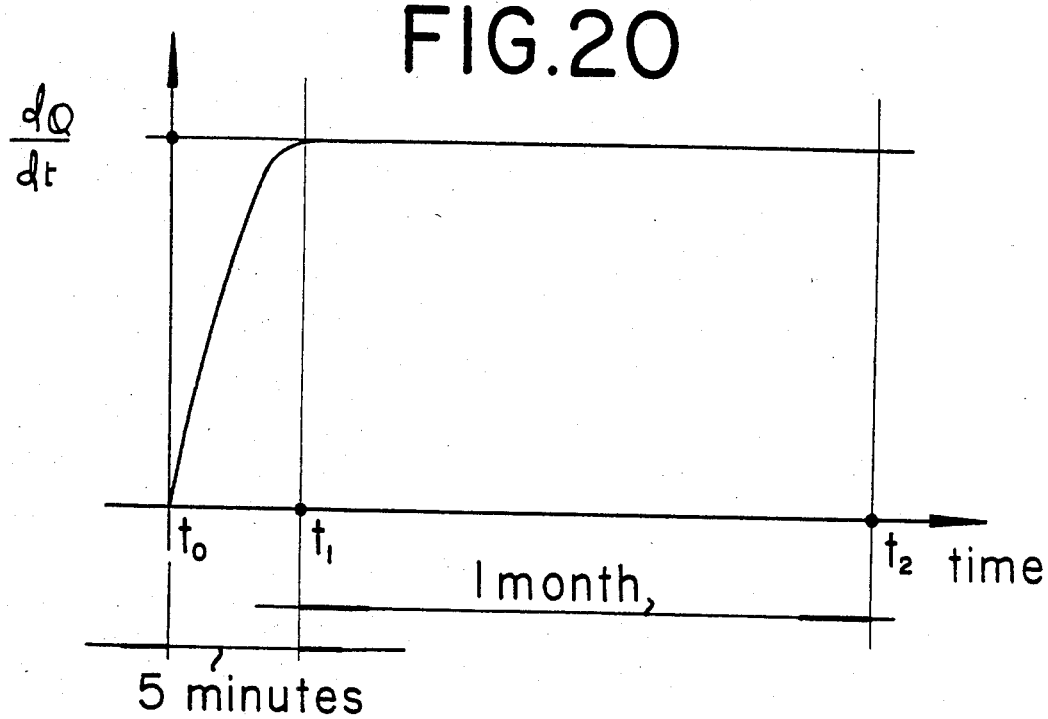
FIG. 20 represents a graph of rate of fragrance loss versus time for the structure of FIG. 1 for up to one month of use.

The process of our invention comprises dispensing continuously (as illustrated in FIG. 20) or discontinuously for discrete periods of time (as shown in FIG. 2) at a constant rate, a volatile composition of matter 3 from a container, e.g., as represented by reference numeral "500" in FIG. 1, into the environment surrounding said container enabled by the use of a polymeric membrane that is defined by having (i) the property of either transporting water vapor at a rate of between about 50 up to about 1000 g/m$^2$/day at about 25° C. and at about 50% relative humidity at about atmospheric pressure and/or having an air transport rate of 100–20,000 Gurley seconds (Gs) and (ii) a thickness in the range of from about 0.01 mils up to about 20 mils.

The steps of this process are exemplified as follows:
(a) providing, and optionally, entrapping a volatile composition of matter which may be a perfume composition, an air freshening composition, a deodorizing composition, an animal repellent composition, an insect repellent composition, an insecticide, a herbicide or a pheromone composition, a composition for the evaluation of olfactory functions in humans or the like (the optional entrapment causing the volatile composition of matter to be entrapped in an entrapment agent whereby a temporarily entrapped volatile composition 3 is formed);

(b) providing a first thin shell section 4 composed of a thin polymeric shell having a curved surface and having an inner void portion, an inner surface and an outer surface and having a first sealable continuous circumferential edge and a first geometric configuration;

(c) placing the volatile composition or entrapped volatile composition 3 in the inner void portion of the first thin shell section and onto the inner surface of the first thin shell section 4;

(d) providing a second thin shell section 2 having a second sealable circumferential edge and a shape and volume which are such that when the second circumferential edge is placed in conforming adjacent edgewise contact with the first sealable circumferential edge, a totally enclosed shell structure 500 is produced with said volatile composition 3 (being optionally entrapped) being totally enclosed within said shell structure leaving a void 6 between said second thin shell section 2 and said volatile substance 3;

(e) placing said second thin shell section 2 having a second sealable continuous circumferential edge which substantially conforms in shape to said first sealable circumferential edge onto said first thin shell section 4 whereby said first sealable edge is in closely fitting sealable proximity with said second sealable edge at location 1;

(f) sealing said first sealable edge of said second sealable edge at location 1 with at least a finite section of the second thin shell section being a microporous polymer membrane having a porosity such that when the hollow totally enclosed structure, now sealed, 500, is located in the ambient environment, said volatile substance is transported at a substantially constant mass flow rate both of the individual volatile components and totally, through said microporous polymer section;

(g) optionally, at time intervals of non-use, or for storage purposes, placing the entire shell structure 500 into an outer container 7 which may or may not be transparent and sealing the opening of the outer container at 8 whereby the outer container 7 is air-tight.

The outer container 7 prevents the escape of the volatile substance from the entrapment medium into the atmosphere prior to the desired operation of the shell structure.

An example of the aforesaid porous polymer composition of matter is as follows:

A microporous polymeric membrane containing a filler having the following specification:

| Composition | Polypropylene + $CaCO_3$ filler |
|---|---|
| Thickness | 100 micrometers |
| Weight | 90 g/m$^2$ |
| Ultimate tensile strength | 30 MN/m$^2$ (machine direction) |
| | 11 MN/m$^2$ (transverse direction) |
| Elongation at break | 180% (machine direction) |
| | 350% (transverse direction) |
| Pore size | 0.2 micrometers (max.) |
| Void volume | 0.34 cm$^3$/g (30%) |
| Density | 900 kg/m$^2$ |
| Air flow | 3 cm$^3$/cm$^2$/min at 1 kg/cm$^2$ |
| Water flow | 0.001 cm$^3$/cm$^2$/min at 1 kg/cm$^2$ |
| Air resistance (Gurley) | 10,000 secs. |
| Water vapour transmission | 150 g/m$^2$/24 hrs. at 23° C. and 50% rh |
| Thermal stability | 10 hrs. at 130° C. | wherein MN is meganewtons, m is meters, g is grams, cm is centimeters and rh is relative humidity.

Additional examples are those where the air resistance (Gurley) varies from about 8000 seconds up to about 12,000 seconds.

The microporous polymer membrane section useful in the practice of our invention has the following specifications:

(i) Water vapor transmission rate: from about 50 up to about 1000 g/m$^2$/day at about 25° C. and at about 50% relative humidity at about atmospheric pressure;

(ii) Porosity range: 100–20,000 Gurley seconds;

(iii) Most preferred porosity range: 8,000–12,000 Gurely seconds;

(iv) Range of Temperature for Operation: From −80° C. up to +150° C.;

(v) Most preferred temperature range of Operation: from 0° C. up to 60° C.; and (vi) A thickness in the range of from about 0.01 mils up to about 20 mils.

Certain statements concerning operation of the microporous polymer membrane of our invention are based upon information disclosed in the paper: "PERMEATION OF PURE GASES UNDER PRESSURE THROUGH ASSYMETRIC POROUS MEMBRANES, MEMBRANE CHARACTERIZATION AND PREDICTION OF PERFORMANCE", Rangarajan, et al, Ind.Eng.Chem. Proc.Des.Dev., 1984, 23, 79–87, the disclosure of which is incorporated by reference herein.

Although a filler is not required insofar as the microporous plymeric membrane is concerned, it is now preferred that a filler be incorporated therein having an average particle size of from about 0.1 up to about 20 micrometers.

Particulate or pulverulent fillers which are useful in the practice of this invention include, but are not limited to clays, including both untreated clays and those which have been surface-treated in various ways well known in art, ground limestone, talc, precipitated calcium carbonate, including surface-treated types, alumina, aluminum silicate, barytes, wollastonite or other calcium silicate, silica, zirconia, titanium dioxide and polymeric fillers such as pulverized phenol resins, polyamides, e.g., nylon 66, polyfluorocarbons, e.g., TEFLON ®, polyesters, e.g., Polyethylene terephthalate, polycarbonates, e.g., LEXAN ®, polyacrylates, e.g., LUCITE ®.

The only limitations are that the fillers should not adversely affect or react with the aromatizing or other functional volatile substance or any entrapping material which may be used in entrapping the aromatizing or other functional volatile substance, or absorb the aromatizing or other functional volatile material to such a degree that release from the microporous polymer membrane is unduly inhibited or entirely prevented. Although the particle size of the filler can be varied over a wide range, e.g., 0.1 micrometers up to 20 micrometers, extremely coarse particles are generally undesirable because they may detract from the physical functioning and mechanical operability of the membrane which is the key functioning member of the apparatus of our invention, as well as the aesthetic qualities of the finished microporous polymeric membrane.

The amount of filler can be varied over a wide range depending on the amount of volatilizing material to be released from the apparatus of our invention or to be released from entrapped volatilizable substance 3, and the viscosity of the volatile vapor being transported. We have found that filler levels in a range of from about 5 up to about 100 parts by weight per 100 parts of polymer are generally satisfactory, although greater or lesser amounts can be used if desired. Indeed, it is not necessary to use any filler so long as the polymeric membrane has (i) the property of either transporting water vapor at a rate of between about 50 up to about 1000 g/m$^2$/day at about 25° C. and at about 50% relative humidity at about atmospheric pressure and/or having an air transport rate of 100–20,000 Gurley seconds (Gs) and (ii) a thickness in the range of from about 0.01 mils up to about 20 mils.

Any type of volatile substance transported, e.g., perfume composition, can be used in the practice of this invention provided that it does not react with any component of the microporous polymer membrane or other substance used in fabricating the structure of our invention. Fragrances are usually complex mixtures and no component of the desired fragrance should be reactive with any component of the microporous polymer membrane or any other component which is used to fabricate the structure of our invention.

When the structure of our invention is ready to be used in dispensing volatile substance at a substantially constant rate, and continuously or discontinuously for discrete periods of time from container 500, the container 500 is removed from outer container 7 and maintained in any convenient area. FIG. 4 illustrates the container 500 in cross section after the volatile material (which may or may not be entrapped in an entrapment agent) is totally depleted as a result of the substantially constant mass transport of the volatile substance through the microporous polymer membrane section of a portion of the container wall. When the volatile substance is entrapped in an entrapment agent, the fully depleted substance is shown in FIG. 4 as indicated by reference numeral "5".

If desired, as an additional embodiment of this invention, each of the shell structures of our invention may be interconnected as shown in FIGS. 11, 12, 13, 14, 15, 16 and 17 as structures 504, 505 and 506. Thus, a plurality of hollow totally enclosed structures, having upper portions 23A, 23B, 23C, 23D, 23E, 23F, 23G, 23H and 23J are laterally and detachably interconnected, having a common midplane 22A, each of said structures being connected to at least two other of said structures, for example in structure 504, at a location midway between the base portion of each of said structures and the upper portion of each of said structures, with the base portion and upper portion of three of said interconnected structures shown in FIG. 12, to wit: the upper portions as 23C, 23D and 23J and the lower portions shown as 29C, 29D and 29J.

In constructing such a structure as structure 504 in FIGS. 11, 12, 13, 14, 15, 16 and 17, the upper polymeric portion containing upper portions 23A, 23B, 23C, 23D, 23E, 23F, 23G, 23H and 23J having a sealable circumferential edge 22A is sealed to a diametrically opposed lower portion containing such lower portions as 29C, 29D and 29J at sealable circumferential edge 22B with sealable circumferential edges 22A and 22B being in closely fitting sealable proximity with one another whereby when they are sealed, an air-tight connection is produced with the only means of ingress and egress from the voids 27C, 27D and 27G for the volatile substances contained in 26C, 26D and 26J being through microporous polymer sections in upper shell portions 23C, 23D, 23J and the like, and/or lower portions 29C, 29D and 29J and the like.

Necessarily, the volatile substance or entrapped volatile substance which would be contained in a gel must not come in direct liquid-solid phase contact with the microporous polymer membrane 23A, 23B, 23C, 23D, 23E, 23F, 23G, 23H and 23J. In order to avoid such a situation, an interposing mesh of much greater porosity than that of the microporous polymer membrane is made part of the construction, e.g., 126J, 126D, 126C, 127J, 127D and 127C and the like. The use of this interposing polymeric mesh may be constructed of polypropylene, for example, and it will enable the creation of embodiments of this invention such as those illustrated in FIGS. 11, 12, 13, 14, 15 and 16.

Figure 13:
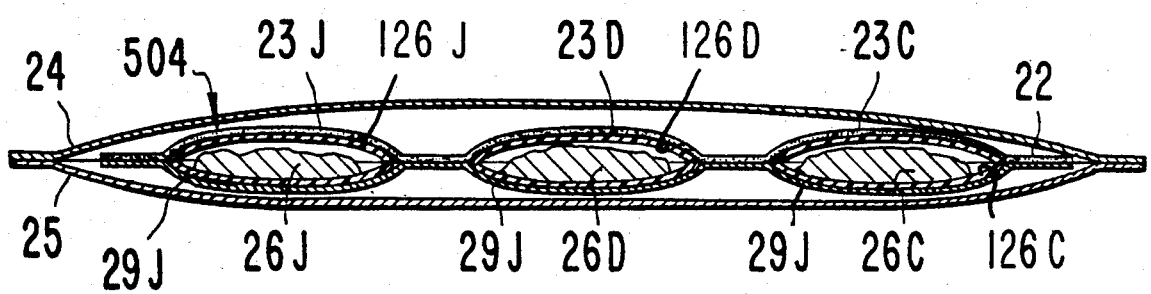
FIG. 13 is an elevation view of the apparatus of FIG. 11 shown in cross section with each of the inter-connected structures of the structure of FIG. 11 fully loaded with volatile substance prior to use, the plurality of inter-connected structures being contained in an air-tight sealed enclosure structure which has a volume greater than the volume of the plurality of inter-connected sealed structures.
Figure 14:
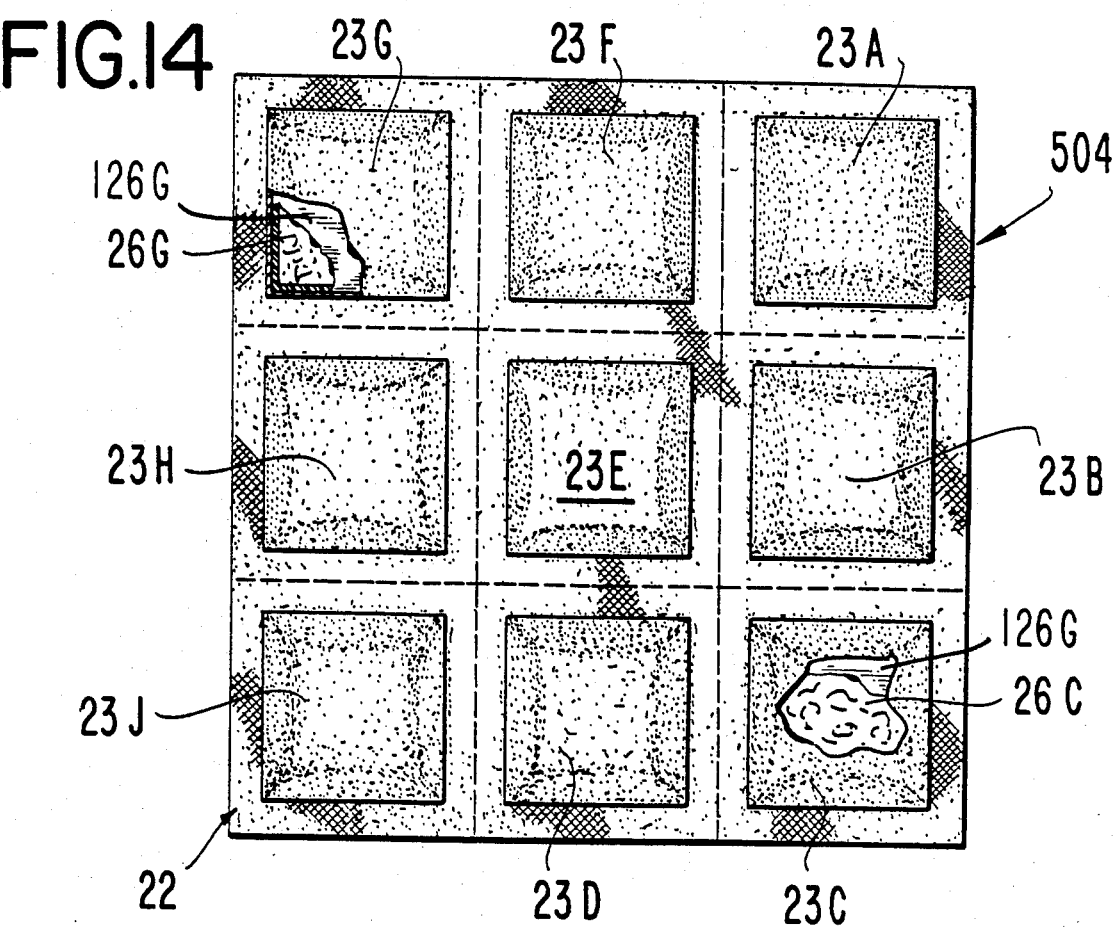
FIG. 14 is a plan view of the plurality of inter-connected structures of FIG. 11.
Figure 15:
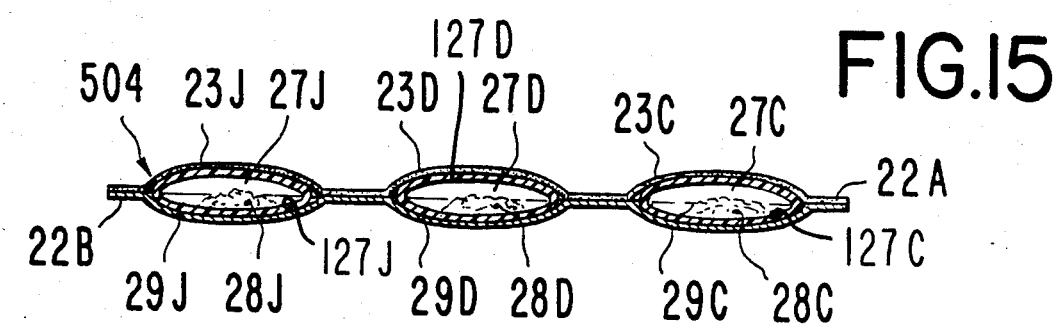
FIG. 15 is an elevation view of the structure of FIG. 11 which is actually a plurality of inter-connected structures (as the individual structure of FIG. 1), with each of the individual structures containing spent volatile substances immediately subsequent to the last functional use of said structure.
Figure 16:
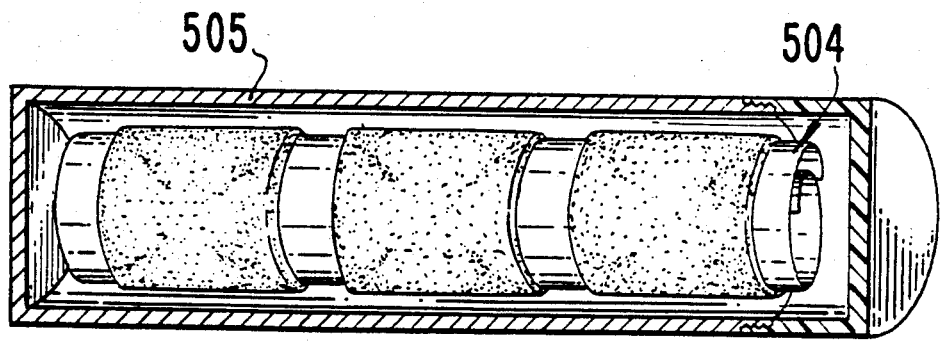
FIG. 16 is a perspective cross-sectional view of the structure of FIG. 11 rolled up and placed in an air-tight cylindrical outer-container when not being used.

Thus, when such a structure as structure 504 as illustrated in FIGS. 11, 12, 13, 14, and 15 are produced, they may be stored while not in use in a container such as container 24 as illustrated in cross section in FIG. 13 or they may be rolled up and stored in container 505 as illustrated in FIG. 16. Conveniently, the container 505 in FIG. 16 is cylindrical in shape and has a closure which is in the form of a screw top which may be easily removed and replaced for the purposes of storing structure 504 while not in use. When structure 504 is stored while not in use, the pressure within container 505 and without structure 504 and within structure 504 is equalized so that during storage no mass transfer from such entrapped volatile substance material as 26C, 26D and 26J takes place into the outer atmosphere.

After the structure 504 is removed from the outer container such as container 24 or container 505, it is then placed in an appropriately convenient place and the volatile substance is depleted from such substances as 26C, 26D and 26J until such point as the substance is totally depleted as illustrated in FIG. 16 (as reference numerals 28C, 28D and 28J).

Figure 17:
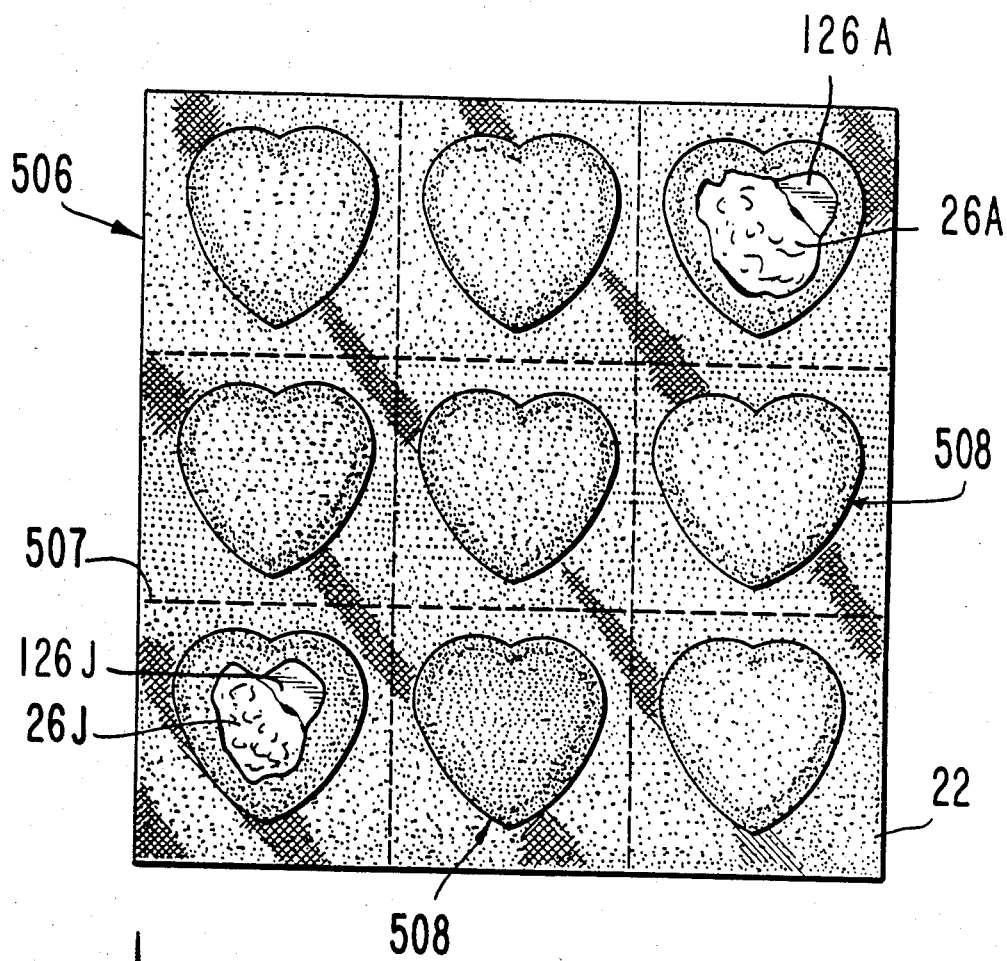
FIG. 17 is a perspective view of another preferred embodiment of our invention wherein a plurality of hollow totally enclosed structures are laterally and detachably inter-connected and have a common mid-plane with each of said structures being connected to at least two other of said structures at a location midway between the base portion of each of said structures and the upper portion of each of said structures and along at least a portion of the circumferential sealed edges of each of said structures sealing said upper portions to said base portions. In the embodiment as set forth in FIG. 17, the shape of the individual structures is "heart"-shaped rather than ellipsoidal in shape.

FIG. 17 illustrates a variation of structure 504 as structure 506 wherein the individual structures may be separated for individual use at 507, with the shape of the upper portion of each of the individual structures indicated as a "heart" shape at 508.

Comparative operation of structure 500 with perfumed fragrance entrapped material or ethyl alcohol entrapped material at 3 with material 3 in prior art apparatus (e.g., that described in U.S. Pat. No. 4,014,501) is set forth in FIG. 18. The graphs shown by reference numerals 201 and 203 represent the operation of structure 500 (percent volatile substance loss versus time) without any perfume material contained within the entrapped volatile substance 3 but only containing ethyl alcohol entrapped in gel 3. The graphs shown by reference numerals 202 and 204 (percent perfume lost versus time) indicate the *rate of release versus time* using structure 500 when employing 2% fragrance in a gel indicated by reference numeral 3. The microporous polymer used in structure 500 has the following specifications:

| | |
|---|---|
| Composition | Polypropylene + filler + CaCO$_3$ |
| Thickness | 100 micrometers |
| Weight | 90 g/m$^2$ |
| Ultimate tensile strength | 30 MN/m$^2$ (machine directon) |
| | 11 MN/m$^2$ (transverse direction) |
| Elongation at break | 180% (machine direction) |
| | 350% (transverse direction) |
| Pore size | 0.2 micrometers (max) |
| Void volume | 0.34 cm$^3$/g (30%) |
| Density | 900 kg/m$^3$ |
| Air flow | 3 cm$^3$/cm$^2$/min at 1 kg/cm$^2$ |
| Water flow | 0.001 cm$^3$/cm$^2$/min at 1 kg/cm$^2$ |

| | |
|---|---|
| Air resistance (Gurley) | 10,000 seconds |
| Water vapor transmission | 150 g/m²/24 hrs at 23° C. at 50% rh |
| Thermal stability | 10 hrs at 130° C. | as manufactured by Koninklijke Emballage Industrie Van Leer B.V. of Amstelveen, The Netherlands.

In each of the graphs wherein perfumed material is used, it is apparent that for the major portion of the useful life of the structure, e.g., structure 500, the rate of mass transport of perfume substance, when in use, is approximately constant, that is:

$$dq/dt = k$$

wherein k is a constant, and q is a measure of the output of volatile substance for the outer surface of the outer polymeric membrane of the article of our invention.

Figure 18:
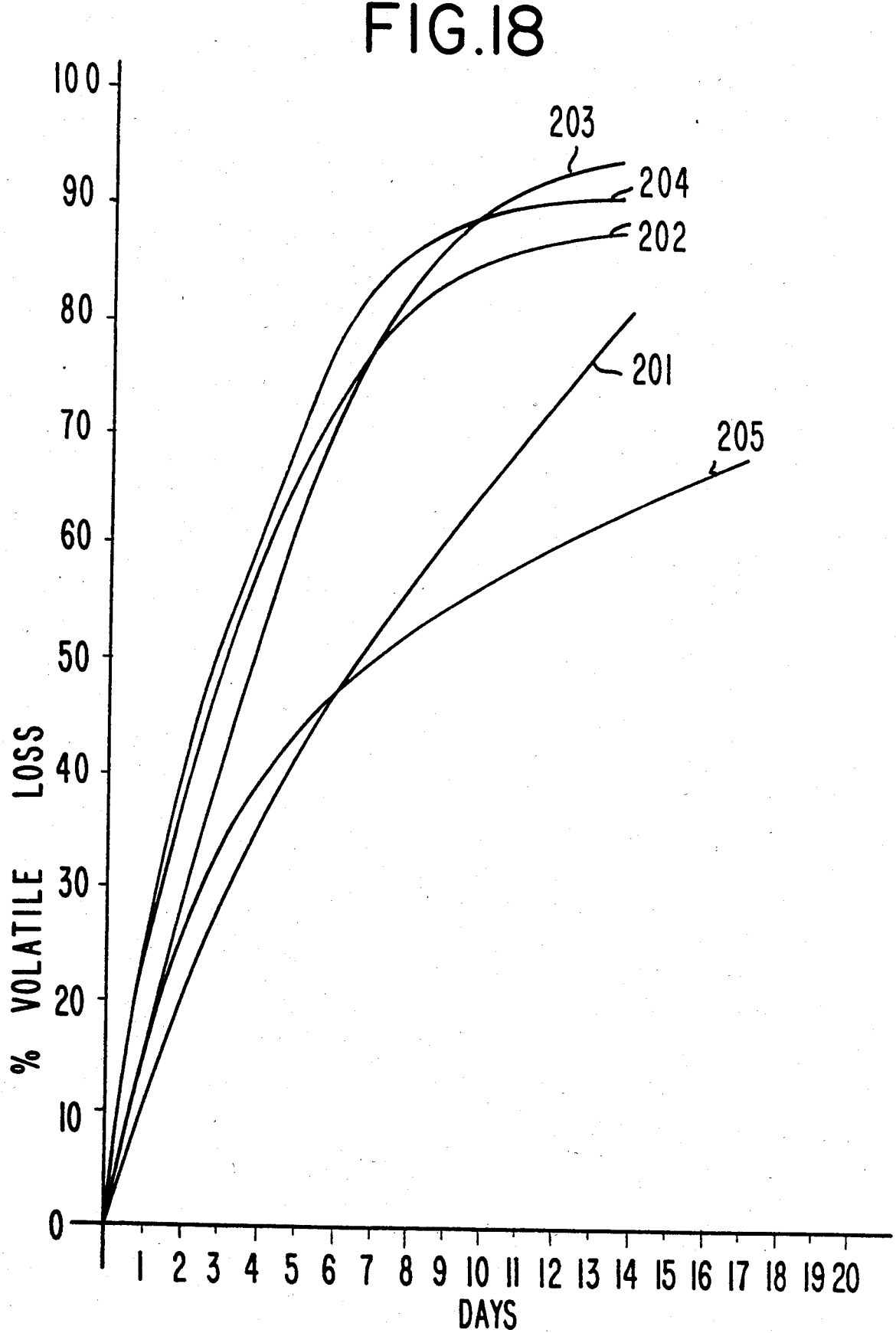
FIG. 18 is a series of graphs of percent volatiles lost versus time comparing the functional use of structures as illustrated in FIG. 1 containing temporarily-entrapped volatilizable substance (air freshener), not containing volatilizable substance (but replaced by ethanol, per se) and standard commercial air fresheners of the prior art as defined according to U.S. Pat. No. 4,014,501. The graphs are more particularly described in Examples I and II(A), infra.

Discussion covering the preparation of the compositions of matter which constitute the fragranced gels and unfragranced gels whereby the graphs as represented by reference numerals 201, 202, 203, 204 and 205 of FIG. 18 are prepared is set forth in Examples I and II(A), infra.

Figure 19:
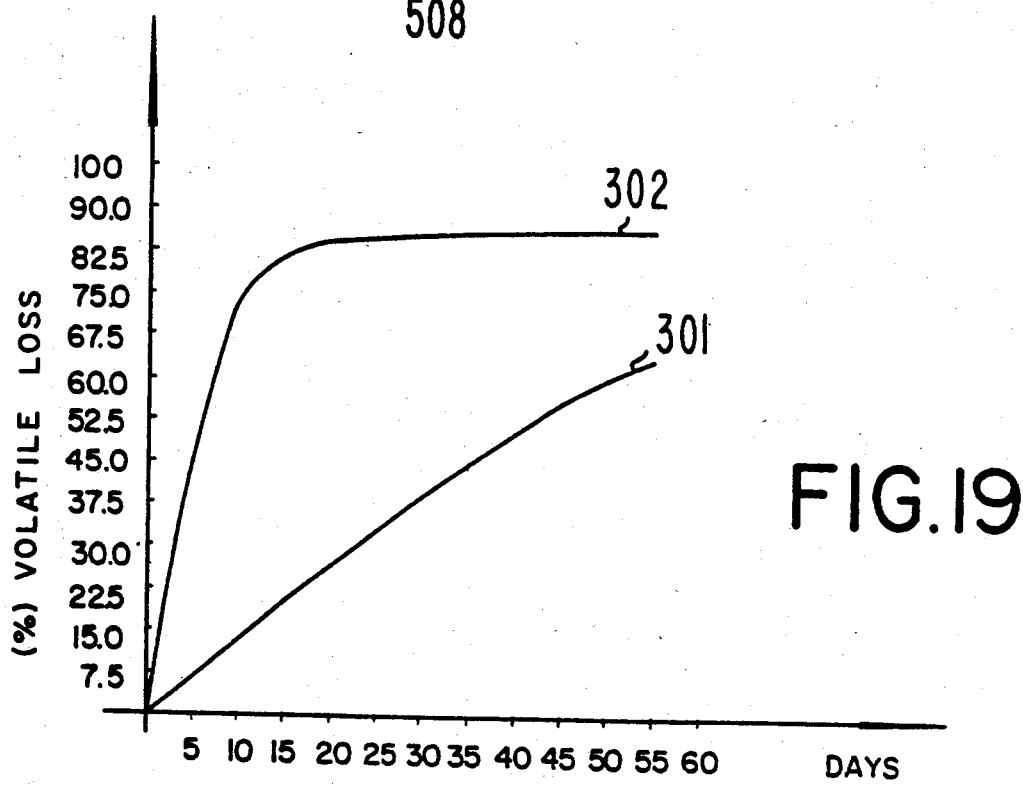
FIG. 19 is a comparative graph showing percent fragrance loss versus time for a structure containing air freshener-containing volatilizable substance as set forth in FIG. 1 versus the same volatilizable substance (air freshener contained in a gel) in the absence of said structure of our invention. (The graph is more particularly described in Example II(B), infra.)

By the same token, in FIG. 19, the graph indicated by reference numeral 302 indicates percent fragrance loss versus time for an air freshener gel containing 2% by weight of fragrance but *not* enclosed in a structure defined according to our invention. It will be noted that the diffusion of aromatizing chemicals or other volatile substances as stated hereinbefore is in accordance with the ordinary diffusion laws and is not steady state, to wit:

$$dq/dt \neq constant$$

Figure 3:
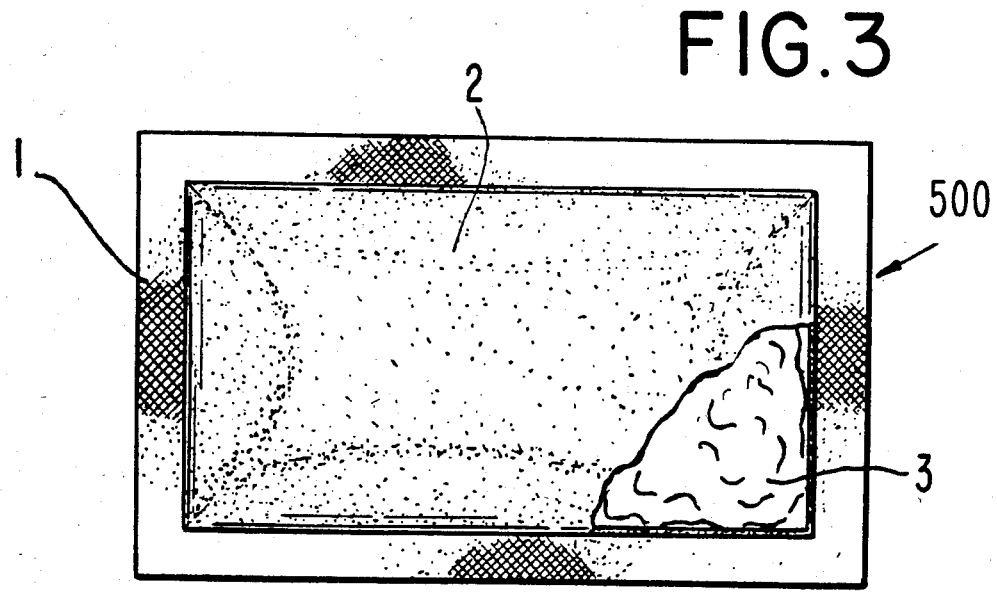
FIG. 3 is a partial cut-away plan view of the structure of FIG. 1 with the structure fully loaded with volatile substance immediately prior to functional use thereof.

On the other hand, the graph indicated by reference numeral 301 in FIG. 19 is for the same air freshener gel 3 containing 2% by weight fragrance (as more particularly described in Example II(B) located in the tin shell structure of our invention as illustrated in FIGS. 1, 2 and 3. The depleted air freshener gel is shown by reference numeral "5" in FIG. 4 (the depletion being at the end of a 55 day period as shown on the graph indicated by reference number "301" in FIG. 19).

Discussion covering the preparation of the compositions of matter which constitute the fragrances and fragranced gels whereby the graphs as represented by reference numerals "410", "411" and "412" in FIG. 41 and reference numerals "420", "421" and "422" in FIG. 42 are prepared is set forth in Example III, infra.

The graph indicated by reference numeral "410" in FIG. 41 indicates mg/cm² evaporated of fragrance where the fragrance is *not* enclosed in a structure defined according to our invention. The graph indicated by reference numeral "411" in FIG. 41 is for the same fragrance (indicated as "EGL-1433") (as more particularly described in Example III) located in the thin shell structure of our invention as illustrated in FIGS. 1, 2, 3 and 5. The graph indicated by reference numeral "412" indicates percent fragrance loss (mg/cm²) vs. time for the same fragrance (EGL-1433) located in a thin shell structure wherein the membrane, rather than being a membrane as defined for use with our invention [(i) having the property of either transporting water vapor at a rate of between about 50 g/m²/day up to about 1000 g/m²/day at about 25° C. and at about 50% relative humidity at about atmospheric pressure and/or having an air transport rate of 100-20,000 Gurley seconds and (ii) having a thickness in the range of from about 0.01 mils up to about 20 mils] uses a polypropylene membrane which has properties including a water transmission property outside of the range of the properties of the membranes useful in our invention.

In FIG. 42, the graph indicated by reference numeral "420" indicates fragrance loss (in mg/cm² evaporated) vs. time for an air freshener gel containing 2% by weight fragrance but not enclosed in a structure defined according to our invention.

The graph indicated by reference numeral "421" is for the same fragrance gel containing 2% by weight fragrance (as more particularly described in Example III) located in the thin shell structure of our invention as illustrated in FIGS. 1, 2 and 3.

The graph indicated by reference numeral "422" in FIG. 42 is for the same fragrance gel containing 2% by weight fragrance (as more particularly described in Example III) located in a thin shell structure of our invention as in FIGS. 1, 2 and 3 wherein the membrane of the structure of our invention is replaced with a polypropylene membrane having an infinite resistance (as being essentially non-porous).

Figure 8:
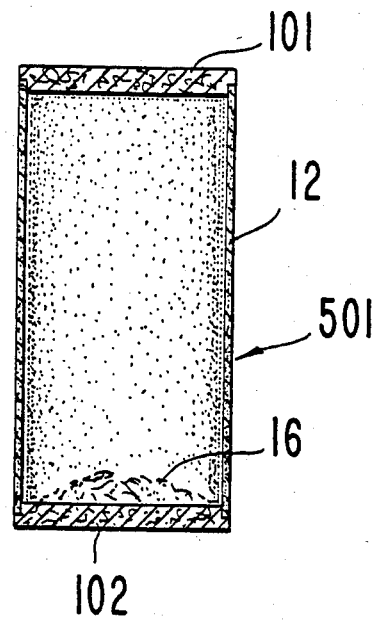
FIG. 8 is an elevation view of the apparatus of FIG. 5 shown in cross section with the volatile substance previously contained in the cylindrical structure having been fully depleted.
Figure 21:
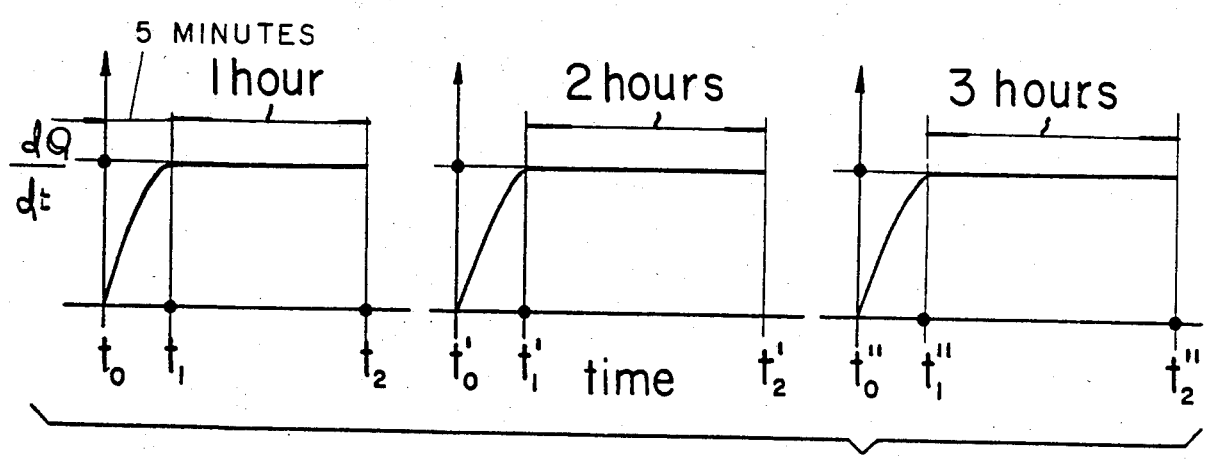
FIG. 21 represents an operational graph of rate of fragrance loss versus time for a structure as shown in FIG. 6 wherein the structure of our invention is removed from an outer container for operation and then replaced in the outer container when not in use and the outer container is resealed when not in use.

FIGS. 20 and 21 show, respectively, continuous and discrete usages of the shell structure as illustrated in FIG. 1. FIG. 20 is a graph of dq/dt versus time; wherein during the first five minutes of operation, the mass transfer rate is described as "*non-steady state*" until a "steady state" condition is reached wherein dq/dt is a constant for at least one month (until depletion as shown in FIGS. 4 and 8).

In FIG. 21, dq/dt is a constant after the first five minutes of usage until the time that the shell structure of our invention as shown in FIG. 1 is placed into an outer container as shown in any one of FIGS. 6, 7 or 16.

FIGS. 22A is a graph of dq/dt versus time (resulting from a "time lag effect") wherein the period of from $t_0'''$ to $t_1'''$ is a condition of "unsteady state" mass transport (usually no more than a few minutes) and the period from $t_1'''$ to $t_w'''$ is a condition of "steady state" mass transport; a very long period of time, e.g., 55-75 days and even longer.

FIG. 22B is a graph of dq/dt versus time (resulting from a "time burst" effect after a build-up—after storage—of fragrance within the hollow totally enclosed structure of our invention) wherein the period of time of from $t_0$ to $t_1$ is a condition of "unsteady state" mass transport (usually no more than a few minutes) and a period of from $t_1$ to $t_2$ is a condition of "steady state" mass transport; a very long period of time e.g., 55-75 days and even longer.

FIG. 22C shows graphs of fragrance loss versus time in the case of a "burst effect" (graph "B") and in the case of a "lag effect" (graph L), further, (reference: Robinson, "Sustained and Controlled Release Drug Delivery Systems", published by Marcel Dekker, Inc., pages 258 and 259 [1978]).

FIGS. 23 and 24 set forth scanning electron microscope photographs of porous polymer membranes filled with $CaCO_3$ filler. FIG. 23 is a photograph showing 500× magnification. FIG. 24 is a photograph showing 3500× magnification.

In FIG. 25, (which is a plot of transport rate of water vapor versus temperature in degrees centigrade), the graph indicated by reference numeral "250" is a graph of transport rate versus temperature for film having a porosity of, nominally, 8000 Gurley seconds.

The graph indicated by reference numeral "253" in FIG. 25 is a graph of transport rate versus temperature in degrees centigrade for rate of water loss from a nominally 12,000 Gurley second filled polypropylene film.

The graph indicated by reference numeral "254" is a graph of transport rate versus temperature in degrees centigrade for rate of water loss from a non-porous, non-filled polypropylene film.

The films as depicted in the graphs in FIG. 25 were placed into diffusion cells as illustrated in FIGS. 28-31 which were loaded with distilled water. The cells were then placed in a constant temperature/humidity oven at 25° C. and 63.5% relative humidity. These conditions provided for a nominal water vapor differential of 10 Torr between the inside and the outside of the cells. After two days, the temperature was adjusted to 35° C. and the relative humidity to 79% providing the same nominal 10 Torr water vapor pressure differential.

FIG. 28 is a perspective view of the diffusion cell which was used in order to obtain the data as set forth in Examples III, IV, V and VI, infra. FIG. 29 is an exploded view of the cell of FIG. 28. Membrane 280 is placed on gland 281 and gland 281 is placed into sealed cap 283 causing the membrane 280 and the gland 281 to be firmly in place and threaded into the sealed cap 283 using lock nut 282. The sealed cap 283 previously has the liquid or gel substance located within it for the purposes of testing the porosity of membrane 280. During the testing, volatile substance passes through membrane 280 into the surrounding atmosphere at 284 as shown in FIG. 30. Sealed cap 283 is shown to be screwed in place using lock nut 282 holding membrane 280 on gland 281 in FIG. 31 and in FIG. 30.

The details concerning FIGS. 26A, 26B, 26C, 27A, 27B as well as FIG. 40 are set forth in Examples V and VI, infra.

Another embodiment which is preferred for the practice of our invention involves the use of a rigid rather than flexible polymer in forming rigid cylindrical containers useful for the process of our invention as illustrated in FIGS. 5, 7, 8, 9 and 10.

The process of our invention for dispensing at a controllable and constant rate, continuously or discontinuously, for discrete periods of time a volatile composition of matter from a cylindrical container 501 into the atmosphere surrounding the container in this particular embodiment comprises the steps of:

A. Entrapping the volatile composition of matter, e.g., perfume, in an entrapment agent (the entrapped material being indicated by reference numeral 11) whereby a temporarily entrapped volatile composition is formed;

B. Placing the entrapped volatile composition 11 within cylinder 501 (that is, a first thin shell section thereto). The top of the cylinder 101 and the bottom of the cylinder 102 may be fabricated from a transparent or translucent non-porous polymer (that is, a polymer which is not porous to the volatilizable substance) whereby a presence of the volatile substance (if accompanied by a color) in the inner void of the cylinder can be detected from the outside of the container so that one can easily ascertain when the entrapped volatile substance 11 is depleted (as shown by reference numeral "16" in FIG. 8). The side wall of the cylinder 12 may be fabricated from a microporous membrane as manufactured by Koninklijke Emballage Industrie Van Leer B.V. and exemplified, supra.

When not in use, the cylinder 501 containing entrapped volatile substance 11 is preferably placed in an outer cylindrical container 502 as shown in FIG. 7. The outer cylindrical container is referred to by reference numeral 502 in FIG. 7. The outer cylindrical container has a removable cap 14 which may be screwed at 103 into the lower portion 13 of said outer container 502. When the cylinder 15 is in use, the screw top 14 is removed and the inner container 15 containing the entrapped volatile composition 11 may remain in place within the outer container 502 or may be removed to a more convenient location for use. Not all of the side wall 12 need be fabricated or microporous polymer. Indeed, merely the upper third or the upper quarter or the lower quarter of the side wall or even the top or the bottom of the cylindrical container may be fabricated from microporous polymer membrane, the remainder of the container 15 shell being fabricated using a translucent or transparent substance which is rigid or flexible or using a silicate or quartz glass.

Figure 9:
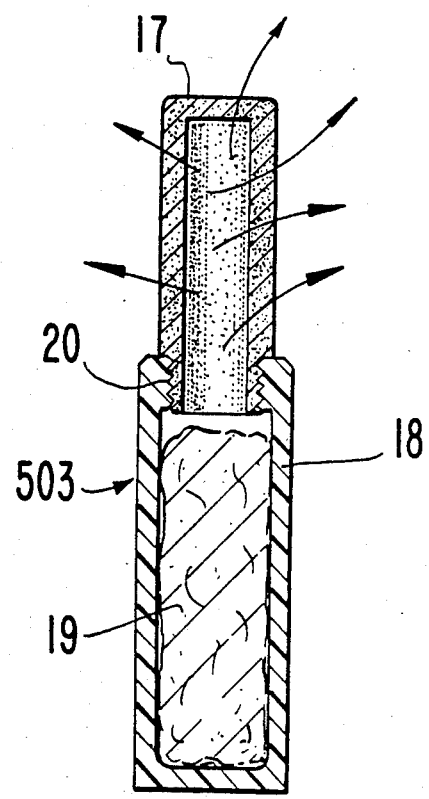
FIG. 9 is an elevation view of another preferred embodiment of our invention, shown in cross section with the volatile substance contained in the structure of our invention being fully loaded in said structure immediately prior to use.
Figure 10:
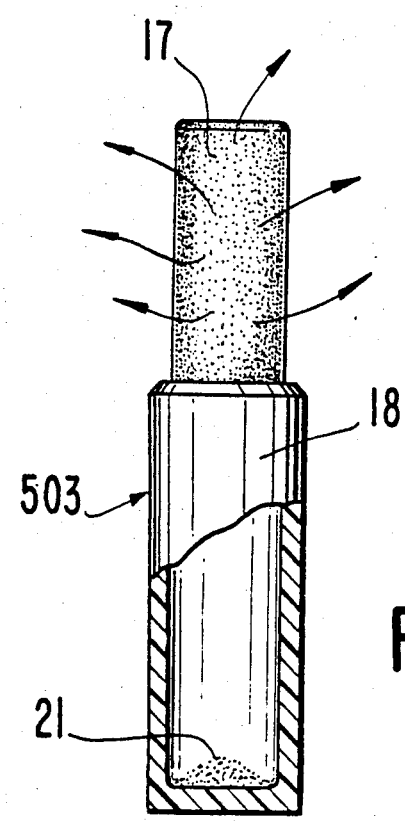
FIG. 10 is an elevation view of the structure of FIG. 9 shown in cross section with the entrapped volatile substance previously contained in said structure having been fully spent.
Figure 11:
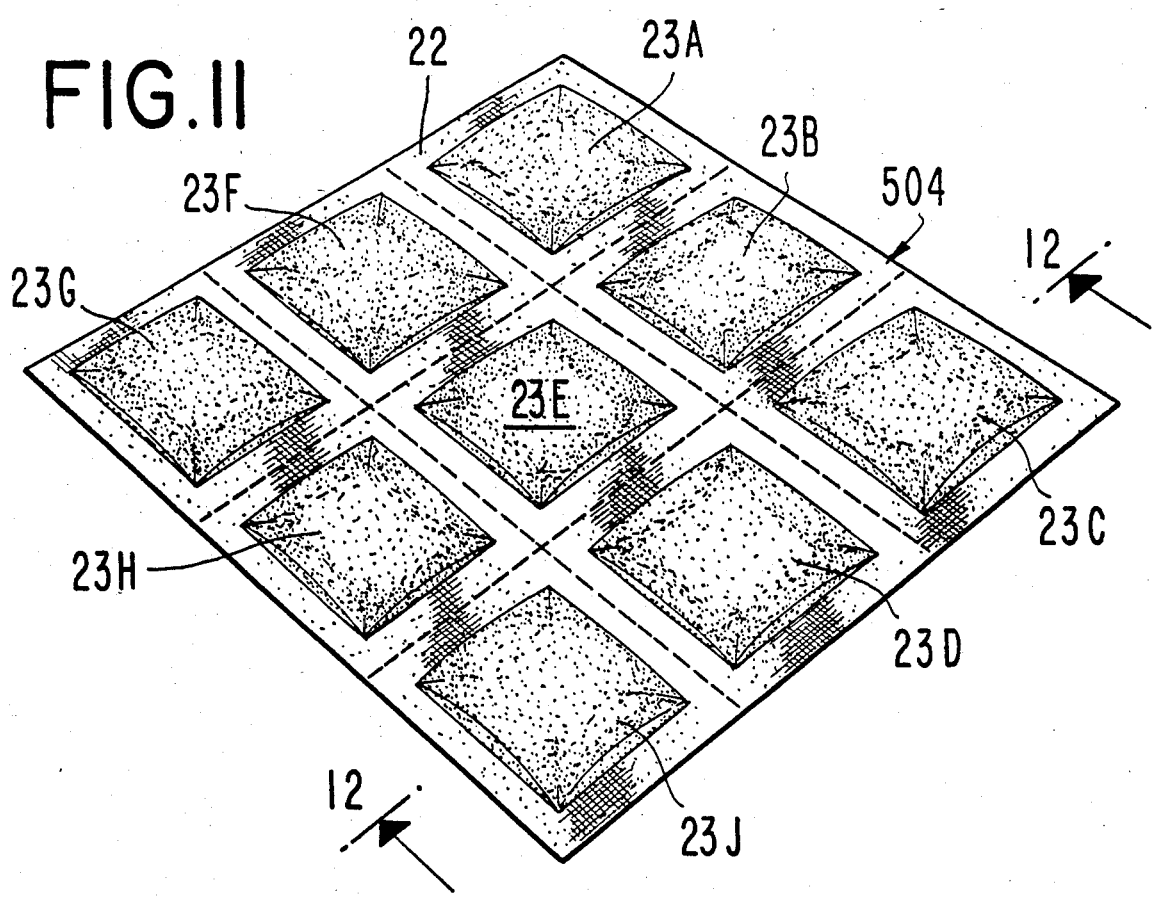
FIG. 11 is a perspective view of a structure in accordance with our invention where multiple structures (as the individual structure of FIG. 1) are connected to one-another at locations midway between the base portions of each of said structures and the upper portions of each of said structures and along at least portions of the circumferential sealed edges of each of said structures which are sealing the upper portion of each of said structures to the base portion of each of said structures.
Figure 12:
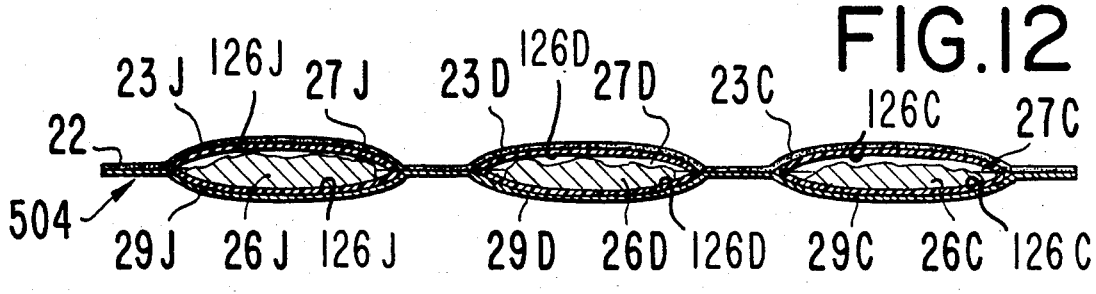
FIG. 12 is an elevation view of the structure of FIG. 11 shown in cross section with each of the individual structures of the inter-connected plurality of structures being fully loaded with volatile substance immediately prior to functional use thereof.

Another embodiment of the cylindrical hollow structure which is illustrative of our invention is set forth in FIGS. 9 and 10 wherein the upper portion of the cylindrical structure 17 may be screwed into the lower portion of the structure 18 at screw threads 20. Thus, structure 503 containing volatile substance 19 may be manufactured in a form which is reusable when the volatile substance 19 is depleted down to the remaining depleted gel (or other entrapment substance) 21 as indicated in FIG. 10. Conveniently, lower portion 18 may be fabricated from a transparent substance such as transparent rigid polypropylene or glass and upper portion 17 may be fabricated from a microporous polymer, e.g., microporous polyurethane or polypropylene containing a filler, e.g., talc or $CaCO_3$.

Thus, when volatile substance 19 is depleted down to depleted substance 21 (as illustrated in FIG. 10), the upper portion 17 of cylinder 503 in FIGS. 9 and 10 may be temporarily removed and additional substance 19 may be added to the lower portion 18. Structure 503 in FIGS. 9 and 10 may then be replaced into a larger cylinder to form a structure such as that illustrated in FIG. 7, the purpose of which is for storage; until it is decided to reuse the structure 503.

The following examples serve to illustrate embodiments of our invention as it is now preferred to practice it with reference to using volatile materials, e.g., air freshener/perfume compositions in conjunction with the hollow totally enclosed structures of our invention as illustrated FIGS. 1, 5, and 9. It will be understood that these examples are illustrative and that the invention is to be restricted thereto only as defined in the appended claims.

EXAMPLE I

Into compartment 6, onto surface 4 of the structure 500 illustrated in FIGS. 1, 2 and 3 is placed a composition prepared as follows: 3.0 parts by weight of Carbopol®940 (manufactured by the B. F. Goodrich Company) (see Note 1) is sifted into the vortex of rapidly stirring water (88.8 parts by weight) containing 0.2 parts by weight of methyl paraben. at a temperature of 22° C. The mixing is continued until a smooth cloudy dispersion is formed. 2.0 parts by weight of a perfume composition (see Note 2) is added to the prepared slurry and the slurry is continued to be mixed until the perfume composition is dispersed. The slurry is then neutralized with 6.0 parts by weight of diisopropanol-amine (50% solution in water) using slow mixing to avoid the inclusion of air. The structure 500 is then sealed along the circumferential edges at location 1 as shown in FIGS. 1, 2 and 3 and use of the structure resulting therefrom is shown in accordance with the graph referenced by reference numeral 202 in FIG. 18. When instead of the perfume (Note 2), only ethyl alcohol is used as the volatilizable material, the operation of structure 500 is in accordance with the graph indicated by reference numeral 201 in FIG. 18. It will be noted that for periods of use, structure 500 operates at steady state very soon after (5 minutes) use is commenced.

Note 1: Carbopol ®940 is produced by the B. F. Goodrich Chemical Company of 3135 Euclid Avenue, Cleveland, Ohio. It is identified as a carboxyvinyl polymer of high molecular weight.

Note 2: The formulation of the fragrance is as follows:

| Ingredients | Parts by Weight |
|---|---|
| Para cresol | 1 |
| Methyl jasmonate | 100 |
| Acetyl methyl anthranilate | 20 |
| Farnesol | 4 |
| Cis-3-hexenyl benzoate | 30 |
| Nerolidol | 30 |
| Indol | 15 |
| Eugenol | 20 |
| Benzyl alcohol | 40 |
| Methyl linoleate | 40 |
| Jasmin lactone | 20 |
| Dihydromethyl jasmonate | 10 |
| Linalool | 150 |
| Benzyl acetate | 400 |
| Abietyl alcohol | 150 |
| Cis jasmone | 150 |

The evaporating surface in hollow structure 500 is 8 square inches; and the weight of entrapped volatile substance 3 is 30 grams.

EXAMPLE II(A)

3.0 parts by weight of Carbopol ®940 (manufactured by the B. F. Goodrich Company) is sifted into the vortex of 44.4 parts rapidly stirring ethyl alcohol and 44.4 parts of distilled water. Mixing is continued until a smooth, cloudy dispersion is formed. 2.0 parts by weight of the perfume of Example I is then added to the prepared slurry and mixing is continued until the perfume is dispersed. The slurry is then neutralized with 6.0 parts by weight of diisopropanolamine (50% solution in water) using slow mixing to avoid inclusion of air at a temperature of 22° C. The resulting gel is then placed into cylinder 500 of FIG. 5. The use of this air freshener cylinder is in accordance with the graph indicated by reference numeral 204 in FIG. 18. Without the use of the perfume composition of Example I, the cylindrical shell of FIG. 5 operates in accordance with the graph indicated by reference numeral 203 in FIG. 18. In both cases, the percent volatiles lost during Example I (but using ethanol, instead), the cylindrical shell of FIG. 5 operates in accordance with the graph indicated by reference numeral 203 in FIG. 18. In both cases, the percent volatiles lost during operation of the cylinder 502 is in accordance with a steady state mass transport mechanism can be observed from the graphs 201, 202, 203 and 204 of FIG. 18.

When the gel of this example is simply used in a commercial air freshener (in the air freshener of U.S. Pat. No. 4,014,501), the mass transport mechanism is "unsteady state" in accordance with the graph indicated by reference numeral 205 in FIG. 18.

EXAMPLE II(B)

83.45 grams of distilled water is heated to 85° C. With rapid agitation on a propeller type mixer, Gelcarin-®AFG-15 (carageenan prepared by the Marine Colloids Corporation) is dispersed in the water. 3.50 grams of glycerine is slowly added to the carageenan dispersion. The mixture of glycerine and carageenan is then reheated and combined with 2.0 parts by weight of the perfume composition of Example I and 8.00 parts by weight of Tween ®80 (a trademark of I.C.I. America) (see Note 3). 0.05 parts by weight of formaldehyde is then added to the resulting mixture slowly and the resulting material is then poured into the cylinder of FIG. 9. It is material is then poured into lower portion 18 of cylinder 503 of FIG. 9. The lower portion 18 of cylinder 503 is then sealed at 20 with upper portion 17 and placed in use.

Note 3: Tween ®80 is a mixture of oleate esters of sorbitol and sorbitol anhydrides consisting predominantly of the monoester condensed with approximately 20 moles of ethylene oxide in accordance with the formula:

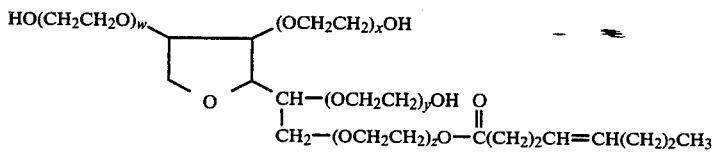

wherein $w+x+y+z$ has an average value of 20.

The graph indicated by reference numeral 301 indicates the length of time of usefulness of the resulting cylinder; a "steady state" mass transport mechanism for the use of cylinder 503 as an air freshening apparatus.

When the composition prepared above is used in accordance with a standard air freshener package (per U.S. Pat. No. 4,014,501), the rate of fragrance loss is shown in accordance with the graph indicated using reference numeral 302 in FIG. 19 (an unsteady state mass transport mechanism rather than the steady state mass transport mechanism of graph 301 in FIG. 19).

EXAMPLE III(A)

Into a group of three jars indicated as (i), (ii) and (iii) each having an opening having an area of of 15.48 cm², a height of 4.2 cm, an opening diameter of 4.4 cm and an internal diameter of 4.8 cm (total volume: 72.5 cc) is placed 5000 mg (5 grams) of the following perfume composition:

| Ingredients | Parts by Weight |
|---|---|
| Citrus oil distilled | 275 |
| Dipentene | 150 |
| The mixture of compounds having the structures: | 130 |

and

-continued

| Ingredients | Parts by Weight |
|---|---|
| prepared according to U.S. Pat. No. 4,330,416 issued on May 18, 1982 (the specification for which is incorporated by reference herein) | |
| Geraniol | 50 |
| Tetrahydro Muguol | 50 |
| Lemon oil | 50 |
| Grapefruit oil | 50 |
| Geranonitrile | 25 |
| n-Octanal | 20 |
| n-Nonanal | 20 |
| n-Decanal | 10 |
| Citronellol | 10 |
| 1-(4-Pentenoyl)-3,3-dimethyl cyclohexane | 25 |
| Beta pinene | 5 |
| n-Nonanol | 20 |
| Cis-3-hexenyl formate | 5 |
| Cis-3-hexanol | 10 |
| Methyl jasmonate | 25 |
| Dihydro methyl jasmonate | 20 |

Jar (i) is left open and the evaporation of the above fragrance formulation is measured on a daily basis.

Jar (ii) is covered in a tight fitting manner with a membrane having the following specifications:

| | |
|---|---|
| Composition | Polypropylene + $CaCO_3$ filler |
| Thickness | 100 micrometers |
| Weight | 90 g/$m^2$ |
| Ultimate tensile strength | 30 MN/$m^2$ (machine direction) |
| | 11 MN/$m^2$ (transverse direction) |
| Elongation at break | 180% (machine direction) |
| | 350% (transverse direction) |
| Pore size | 0.2 micrometers (max) |
| Void volume | 0.34 $cm^3$/g (30%) |
| Density | 900 kg/$m^3$ |
| Air flow | 3 $cm^3/cm^2$/min at 1 kg/$cm^2$ |
| Water flow | 0.001 $cm^3/cm^2$/min at 1 kg/$cm^2$ |
| Air resistance (Gurley) | 8,000 seconds |
| Water vapor transmission | 150 g/$m^2$/24 hrs at 23° C. at 50% rh |
| Thermal stability | 10 hrs at 130° C. |

Jar (iii) is covered in a tight fitting manner with a polypropylene film of 1 mil thickness. In each of the jars the rate of evaporation of the fragrance is measured on a daily basis. The weight loss occurs at constant temperature, 22° C. and constant relative humidity, 50% relative humidity.

Table I set forth below shows weight loss as a function of time and weight loss per square centimeter as a function of time for each of jars (i), (ii) and (iii).

TABLE I

| | JAR (i) | | JAR (ii) | | JAR (iii) | |
|---|---|---|---|---|---|---|
| Days | Mg of perfume composition lost | mg/$cm^2$ of perfume composition lost | Mg of perfume composition lost | mg/$cm^2$ of perfume composition lost | Mg of perfume composition lost | mg/$cm^2$ of perfume composition lost |
| 1 | 130 | 12.3 | 80 | 5 | 20 | 1.3 |
| 2 | 470 | — | 150 | — | 50 | — |
| 3 | 630 | 45.0 | 230 | 15 | 80 | 5.0 |
| 6 | 1070 | 69.0 | 370 | 24 | 120 | 8.0 |
| 7 | 1330 | — | 430 | — | 140 | — |
| 9 | 1850 | 119.0 | 560 | 36 | 200 | 13.0 |
| 15 | 2310 | 149.0 | 880 | 57 | 310 | 20.0 |
| 31 | 2660 | 172.0 | 1450 | 94 | 600 | 39.0 |
| 36 | 2740 | 177.0 | 1560 | 100 | 680 | 44.0 |

The series of graphs set forth in FIG. 41 indicates graphically the results set forth in Table I, supra. Thus, the graph indicated by reference numeral "410" is the graph for the rate of fragrance composition evaporation from Jar (i). The graph indicated by reference numeral "411" is the graph for the rate of evaporation of fragrance composition from Jar (ii). The graph indicated by reference numeral "412" on FIG. 41 is the graph for the rate of evaporation of fragrance composition from Jar (iii).

EXAMPLE III(B)

Three jars are provided, Jar (iv), Jar (v) and Jar (vi) having dimensions identical to those of Example III(A). To each of the jars, 20 grams of a perfumed gel is added which is prepared as follows:

"3.0 parts by weight of Carbopol ®940 (manufactured by the B. F. Goodrich Company) (see Note 1 of Example I) is sifted into the vortex of rapidly stirring water (88.8 parts by weight) containing 0.2 parts by weight of methyl paraben at a temperature of 22° C. The mixing is continued until a smooth cloudy dispersion is formed. 2.0 Parts by weight of the perfume composition of Example III(A) is added to the prepared slurry and the slurry is continued to be mixed until the perfume composition is dispersed. The slurry is neutralized with 6.0 parts by weight of diethylpropenol-amine (50% solution in water) using slow mixing to avoid the inclusion of air."

Jar (iv) is permitted to remain open while measurements for weight loss of gel are made on a daily basis.

Jar (v) is tightly covered with a membrane having the same specifications as the membrane used to cover Jar (ii) in Example III(A) and the weight loss is measured on a daily basis.

Jar (vi) is covered with a polypropylene film having a thickness of 1 mil and the weight loss of the gel is measured on a daily basis.

Table II, below sets forth weight loss as measured in mg/$cm^2$ for each of Jars (iv), (v) and (vi):

TABLE II

| Days | JAR (iv) (mg/$cm^2$) | JAR (v) (mg/$cm^2$) | JAR (vi) (mg/$cm^2$) |
|---|---|---|---|
| 1 | 134 | 28 | 0.7 |
| 3 | 555 | 113 | 2.0 |
| 6 | 1007 | 219 | 2.0 |
| 9 | 1201 | 349 | 3.9 |
| 15 | 1207 | 570 | 4.5 |
| 31 | 1210 | 1083 | 9.0 |
| 36 | 1209 | 1154 | 9.7 |

FIG. 42 is a graphical representation of the results set forth in Table II, supra. The graph indicated by reference numeral "420" is the graph for the open jar, Jar (iv) (mg/$cm^2$ vs. time). The graph indicated by reference numeral "421" is the graph for the weight loss of gel from Jar (v). The graph indicated by reference numeral "422" is the graph for the weight loss of gel from Jar (vi) as a function of time.

EXAMPLE IV(A)

The following experimental design was established through an evolutionary process in order to determine the permeability of water vapor through filled polypropylene film as exemplified, supra.

I. Cell Design

Stainless steel 316 diffusion cells as illustrated in FIGS. 28–31, inclusive the details for which are set forth, supra, were specially designed to measure the transport of small amount of water vapor through a film sample under controlled experimental conditions. Commercially available fittings (nut, plug and glands) were modified to accommodate water or a volatile substance in one side of the gland and a film specimen between the two glands.

II. Materials

Films: A film designated as having a nominal air transport rate of 12,000 Gurley seconds (Gs) was employed. Six samples, each measuring 6"×6", were cut from the center of a 10" wide stock sample. From each of these test samples, a sample approximately 2.0 cm in diameter was used for the permeation experiments and a sample of approximately 5" diameter was used for air permeation measurements. Approximately 0.5 g of water were used in each of the test cells.

III. Environmental Conditions

A. Oven:

A Blue "M" controlled temperature and humidity oven was used for all experimental conditions. The temperature and humidity conditions were controlled by the dry and wet bulb thermometers located inside of the test chamber.

B. Conditions:

The following conditions were used in the experiments:

| Temperature (°C.) | 25 | 30 | 35 | 40 | 45 | 50 | 55 |
|---|---|---|---|---|---|---|---|
| Relative Humidity (%) | 50 | 63 | 72 | 78.5 | 83.5 | 89 | 90 |

These conditions established a relative water vapor pressure difference of 15.85 mb between the inside and outside of the cell.

C. Temperature conditions:

The following sequences of temperatures (°C.) were employed to randomize the sample treatments and reduce possible systematic error:

(A) 25 - 45 - 30 - 40 - 55 - 35 - 25 - 35° C.
(B) 35 - 50 - 30 - 45 - 25 - 35 - 40 - 25 - 30° C.

IV. Sample Weighing

The cells were placed in the oven at the selected temperature condition so that the film was in the "up" position as indicated in FIGS. 30 and 31. After the samples were equilibrated for at least 10–12 hours, the samples were weighed using a Mettler AE-163 electronic balance interfaced to the Digital Equipment Corporation (Maynard, Mass.) VAX®11/780 computer.

The samples were then replaced in the oven and were reweighed after approximately 12 hours to give the transport rate for each condition. Five replicates were run and samples were re-tested at 25°, 30° and 35° C. to monitor reproducibility.

EXAMPLE IV(B)

The following Table III shows the air resistance rating of 15 films measured in Gurley seconds and the minimum and maximum water transport rates that were observed at 25° C. and at 50% relative humidity. The measurements were carried out using cells and procedures substantially as described in Example IV(A), supra.

TABLE III

| | WATER TRANSPORT AT 25° C. | | |
|---|---|---|---|
| Film No. | Air Resistance (Gurley seconds) | Minimum Water Transport Rate (g/m²/day) | Maximum Water Transport Rate g/m²/day |
| 1 | 1600 | 370 | 683 |
| 2 | 2100 | 508 | 667 |
| 3 | 3100 | 434 | 603 |
| 4 | 3200 | 249 | 593 |
| 5 | 3300 | 439 | 651 |
| 6 | 4000 | 376 | 481 |
| 7 | 4300 | 339 | 751 |
| 8 | 4300 | 413 | 677 |
| 9 | 5400 | 143 | 481 |
| 10 | 6000 | 140 | 344 |
| 11 | 6700 | 243 | 333 |
| 12 | 7000 | 249 | 608 |
| 13 | 7100 | 222 | 280 |
| 14 | 10200 | 222 | 317 |
| 15 | 10800 | 169 | 193 |

EXAMPLE V

Materials

A. TEST PRODUCTS: Eight samples of articles as illustrated in FIG. 5.

B. TEST CHAMBERS: The test chambers were constructed from white polypropylene canisters of 5 gallon liquid volume which has been fitted with an air-tight lid. The lid had a 2 inch evaluation hole cut in the middle which was fitted with a cork stopper. Individual samples were placed in the chambers approximately 1 hour prior to evaluation to permit equilibration.

C. JUDGES: A panel of 23 individuals trained and skilled in the practice of magnitude estimation were employed as odor intensity judges. The judges provided ratio-scaled assessments of the perceived odor intensity.

D. CONTROL SAMPLES: The following control samples were incorporated into the experimental design:

1. 100 g. Unfragranced Gel, fully exposed from a petri plate, the gel being prepared in accordance with the process of Example III(B).
2. 100 g. Fragranced Gel ("894m"), fully exposed from a petri plate (prepared according to the procedure of Example III(B).

E. SAMPLE EXPOSURE: Duplicate samples were scheduled for ambient room exposure based upon a converging depletion design so that samples representing 0, 2, 3, and 4 weeks of exposure were available at the date of the sensory test.

Methods

All exposed samples were submitted in the blind to the panel of judges after 1 hour in the test chambers. A total of 22 samples were evaluated in the test. All test samples were randomized upon submission to the judges and re-randomized periodically throughout the evaluation period.

The magnitude estimation sensory data (Reference: Warren, C. B., Paper #3 "Development of Fragrances With Functional Properties by Quantitative Measurement of Sensory and Physical Parameters", Moskowitz & Warren "Odor Quality and Chemical Structure", ACS Symposium Series 148 (American Chemical Society, Washington, D.C. 1981) was normalized by the method of "no standards". Standard errors of the measurements were calculated to determine the significance of the perceived test sample intensities.

Analytical Data

The cumulative weight-loss was obtained during the exposure period for each of the test samples (excluding the controls and the zero-time samples). The periodic weighings were compiled and reported as Cumulative Weight-loss vs. time and this is shown in FIGS. 26A, 26B and 26C.

Results

The summarized sensory testing results are presented for fragrance "894m" in Table IV, infra. The normalized product weight-loss data for "894m" are incorporated into the last two columns of this Table (IV) and reported graphically in FIGS. 26A, 26B and 26C.

The graph indicated by reference numeral "260" is the graph showing grams loss of gel vs. time for four weeks of exposure of gel containing fragrance "278m".

The graph indicated by reference numeral "262" is the graph showing the mean weight loss after 4 weeks of exposure for the gel containing fragrance "894m".

The graph indicated by reference numeral "264" is the graph showing the mean weight loss rate for gel containing fragrance "278m" after 3 weeks.

The graph indicated by reference numeral "263" is the graph showing the mean weight loss of a gel containing fragrance "894m" after 3 weeks.

The graph indicated by reference numeral "265" is the graph showing the mean weight loss of a fragranced gel containing fragrance "278m" after 2 weeks exposure.

The graph indicated by reference numeral "261" is the graph of the mean weight loss of a gel containing fragrance "894m" after 2 weeks exposure.

Graphs 260, 264 and 265 are shown separately on FIG. 26B.

Graphs 261, 262 and 263 of FIG. 26A are shown separately in FIG. 26C.

Discussion

The results of the sensory experiments suggest that there is a critical equilibration point sometime between "zero" and 2 weeks. This is reflected in the intensity decay between these two evaluation points in this experiment.

The product containing fragrance "894m" did not show any significant percevied odor intensity decay over the period of 2 thru 4 weeks of exposure.

Summary

The results of this study indicate that the product fragranced with "894m" quickly equilibrates to what is perceived as a "steady-state" fragrance delivery rate over a 4 week period.

TABLE IV

Quantitative of Odor Evaluation of Fragrance "894 m" by Magnitude Estimation

Fragrance: "894 m"
No. of Panelists: 23

| Sample Indent | Exposure Time | Mean Intensity[b] | Std. Error[a] | Average Intensity | Std. Error[a] | mg/hr. Frag. Loss Nom. | / Ave. |
|---|---|---|---|---|---|---|---|
| Control Fragranced Gel | 0 hrs. | 80.3 | 1.05 | 78.89 | 1.04 | — | — |
|  |  | 77.5 | 1.05 |  |  |  |  |
| Zero Time | 16 hrs. | 53.1 | 1.13 | 52.87 | 1.08 | — | — |
|  |  | 52.6 | 1.10 |  |  |  |  |
| 2 Weeks | 319 | 43.0 | 1.07 | 43.94 | 1.06 | 66.4 | 67.6 |
|  |  | 44.9 | 1.10 |  |  | 66.7 |  |
| 3 Weeks | 482 | 51.1 | 1.05 | 45.83 | 1.06 | 54.2 | 55.0 |
|  |  | 41.1 | 1.12 |  |  | 55.8 |  |
| 4 Weeks | 646 | 36.1 | 1.09 | 45.36 | 1.05 | 59.5 | 62.6 |
|  |  | 57.0 | 1.05 |  |  | 65.8 |  |

[a]Geometric means are calculated for all intensities. Standard errors should be read as 1. + % error, e.g., 1.13 = 13% relative error.
[b]A moderate odor intensity has a value of 30 on this scale.

EXAMPLE VI

Air Freshener Products

Materials

Air fresheners produced according to Example V and used in said Example V were then utilized for this example.

GLC analysis was peformed on dual 50 meter fused silica capillary columns containing OV-1 or Carbowax 20M liquid phases.

METHODS

Aliquots of the test samples were prepared for analysis by placing 5 grams of sample, in a shaker jar with 25 ml of food grade ethanol and shaking on a wrist-action shaker for approximately 24 hours until no additional color could be removed from the gelatinous residue. The ethanol solution was quantitatively decanted and the gelatinous residue was washed with an additional 10 ml of food grade ethanol. The extract and wash were combined, diluted volumetrically to 50 ml and filtered using a Millipore ® filter.

RESULTS

GLC analysis of the isolates confirmed that the profile of the isolate was consistent with that of the original fragrance oil.

The results of the internal standard GLC analyses are presented (a) for fragrance 278m on Carbowax 20M in FIGS. 32 (0 weeks), 33 (2 weeks), 34 (3 weeks) and 35 (4 weeks) and (b) for 894m on Carbowax 20M in FIG. 36 (0 weeks), 37 (2 weeks), 38 (3 weeks) and 39 (4 weeks).

FIG. 40 sets forth a dual graph of weight loss vs. time for 278m (as shown by the graph indicated by reference numeral "401") and for odor intensity on a scale of 0 to 30 units as shown by the graph indicated by reference numeral "402".

Discussion

The isolates were subjected to internal standard capillary GLC to confirm/sensory evaluation. In comparing the GLC results across the 4 week period, it is obvious that there is apparent disproportionation of the fragrance over the 4 week exposure period.

What is claimed is:

1. A hollow totally enclosed structure capable of the release into the space surrounding said structure at a substantially constant rate of at least one volatile consumable material consisting of volatile consumable material molecules, said volatile consumable material being selected from the group consisting of: perfume compositions, herbicide compositions, insecticide compositions, animal repellent compositions, air freshener compositions, pheromone compositions, odor maskant compositions, deodorant compositions, insect repellent compositions and compositions for the evaluation of olfactory funtioning in humans; said structure comprising (i) a thin shell totally enclosing an inner void with at least a first finite section of said thin shell being a microporous polymer shell section consisting of a porous membrane having (1) the property of transporting water vapor at a rate of from about 50 g/m$^2$/day up to about 1000 g/m$^2$/day at about 25° C. and at about 50% relative humidity at about atmospheric pressure and having an air transport rate of 100-20,000 Gurly seconds (Gs) and (2) a thickness in the range of from about 0.01 mils up to about 20 mils; the remaining second section of said thin shell having a porosity equal to or less than the porosity of said first finite section, said microporous polymer shell section consisting essentially of a polyolefin intimately admixed with a powder having an air transport rate of 100-20,000 Gurley sec- up to about 500 microns, said powder being a filler material incompatible with said polymer, said powder being in a proportion of from about 5 to 100 parts by weight per 100 parts by weight of polymer, the said volatile composition having a volatility at ambient conditions which is higher than the transmissibility of said microporous polymer shell section, and (ii) located within said inner void on a portion of said second section, said volatile consumable material, releasably entrapped in a gel.

2. The hollow totally enclosed structure of claim 1 wherein the polyolefin and the microporous polymer shell section in polypropylene; the thickness of the microporous polymer shell section is about 100 micrometers; the pore size of the polypropylene is approximately 0.1 micrometers; the void volume of the polypropylene is approximately 34 cubic centimeters per 100 grams and the density of the polypropylene is approximately 900 kilograms per cubic meter.

3. A plurality of hollow totally enclosed structures laterally and detachably interconnected having a common midplane, each of said structures being defined individually according to claim 2 each of said structures connected to at least one other said structures (i) at a location midway between the base portion of each of said structures and the upper portion of each of said structures and the upper portion of each of said structures and (ii) along at least a portion of the circumferential sealed edge of each of said individual structures sealing said upper portion to said base portion of each of said individual hollow totally enclosed structures.

4. A hollow totally enclosed structure which is capable of controllable functional operation for the controlled release into the space surrounding said structure of at least one volatile consumable material selected from the group consisting of perfume compositions, herbicide compositions, insecticide compositions, animal repellent compositions, air freshener compositions, pheromone compositions, odor maskant compositions, deodorant compositions, insect repellent compositions and compositions for the evaluation of olfactory functioning in humans, comprising (i) a thin shell totally enclosing an inner void, said thin shell having an inner surface and an outer surface, the inner surface thereof being the boundary of said inner void, said thin shell having a base portion and an upper portion, said base portion having an inner surface:

(a) contained totally within the inner void of said thin shell and in place on said inner surface of said base portion, a volatile composition existing in the liquid state at ambient conditions temporarily entrapped and totally entrapped in an entrapment material at least at the instant in time of commencement of functional operation of said structure, said volatile composition being selected from the group consisting of perfume compositions, herbicide compositions, insecticide compositions, animal repellent compositions, air freshener compositions, pheromone compositions, odor maskant compositions, deodorant compositions, insect repellent compositions and compositions for the evaluation of olfactory functioning in humans; and (b) at least a finite section of said thin shell consisting of a microporous polymer membrane section having an inner surface and an outer surface, and having (i) the properties of transporting water vapor at a rate of from about 50 g/m$^2$/day up to about 1000 50 g/m$^2$/day at about 25° C. and at about 50% relative humidity at about atmospheric pressure and having an air transport rate of 100-20,000 Gurley seconds (Gs) and (ii) a thickness in the range of from about 0.01 mils up to about 20 mils, said microporous polymer membrane section having a porosity such that when said hollow totally enclosed structure is located in the ambient environment at a point in time substantially immediately or subsequent to the commencement of functional operation of said structure and thereafter in a controllable time release manner, said volatile material molecules are transported at a constant mass flow rate both of the individual volatile components and totally through said microporous polymer membrane section, said microporous polymer membrane section consisting essentially of a polyolefin intimately admixed with a powder having an average particle diameter of from about 0.3 up to about 500 microns, said powder being a filler material incompatible with said polymer, said powder being in a proportion of about 5 to 100 parts by weight per 100 parts by weight of polymer, the said volatile composition having a volatility at ambient conditions which is higher than the transmissibility of said microporous polymer membrane section, and (ii) located within said inner void on said base portion of said thin shell, said volatile consumable material releasably entrapped in a gel.

5. A structure defined according to claim 4 wherein (i) said base portion comprises a first thin polymer shell having a curved surface and an inner void portion and an inner surface and an outer surface and a first sealable continuous circumferential edge; (ii) said upper portion comprises a second thin shell section having a second sealable continuous circumferential edge which substantially conforms in shape to said first sealable circumferential edge and (iii) said base portion is sealed by means of a continuous seal at the first circumferential edge thereof to said upper portion at the said second circumferential edge thereof.

6. A process for providing an environment with a volatile consumable material selected from the group consisting of perfume compositions, herbicide compositions, insecticide compositions, animal repellent compositions, air freshener compositions, pheromone compositions, odor maskant compositions, deodorant compositions, insect repellent compositions and compositions for the evaluation of olfactory functioning in humans comprising the step of placing a hollow totally enclosed structure capable of the release into the space surrounding said structure at a substantially constant rate of at least one of said volatile consumable materials, said structure comprising (i) a thin shell totally enclosing an inner void with at least a first finite section of said thin shell being a microporous polymer shell section consisting of a porous membrane having (1) the property of transporting water vapor at a rate of from about 50 g/m$^2$/day up to about 1000 g/m$^2$/day at about 25° C. and at about 50% relative humidity at about atmospheric pressure and having an air transport rate of 100–20,000 Gurley seconds (Gs) and (2) a thickness in the range of from about 0.01 mils up to about 20 mils; the remaining second section of said thin shell having a porosity equal to or less than the porosity of said first finite section, said microporous polymer shell section consisting essentially of a polyolefin intimately admixed with a powder having an average particle diameter of from about 0.3 up to about 500 microns, said powder being a filler material incompatible with said polymer, said powder being in a proportion of about 5 to 100 parts by weight per 100 parts by weight of polymer, the said volatile composition having a volatility at ambient conditions which is higher than the transmissibility of said microporous polymer shell section, and (ii) located within said inner void on a portion of said second section, said volatile consumable material initially releasably entrapped in a gel, in said environment and permitting the resulting system to equilibrate.

7. A hollow totally enclosed structure capable of controllable functional operation for the controlled release into the space surrounding said structure of at least one consumable material selected from the group consisting of perfume compositions, herbicide compositions, insecticide compositions, animal repellent compositions, air freshener compositions, pheromone compositions, odor maskant compositions, deodorant compositions, insect repellent compositions and compositions for the evaluation of olfactory functioning in humans comprising (i) a thin shell totally enclosing an inner void, said thin shell having an inner surface and an outer surface, the inner surface thereof being the boundary of said inner void, said thin shell having a base portion and an upper portion, said base portion having an inner surface:

(a) contained totally within the inner void of said thin shell and in place on said inner surface of said base portion, a volatile composition existing in the liquid state at ambient conditions temporarily entrapped and totally entrapped in an entrapment material at least at the instant in time of commencement of functional operation of said structure, said volatile composition being selected from the group consisting of perfume compositions, herbicide compositions, insecticide compositions, animal repellent compositions, air freshener compositions, pheromone compositions, odor maskant compositions, deodorant compositions, insect repellent compositions and compositions for the evaluation of olfactory functioning in humans;

(b) at least a finite section of said thin shell section consisting of a filled microporous porous shell section consisting essentially of (1) a porous polymer lamina and (2) in random admixture with said polymer lamina a filler dispersed in the pores of said polymer lamina, said filler being in the solid phase, said filler being in a phase separate from the polymer phase of the polymeric lamina having an inner surface and an outer surface, and having (i) the property of transporting water vapor at a rate of between about 50 g/m$^2$/day up to about 1000 g/m$^2$/day at about 25° C. and about 50% relative humidity at about atmospheric pressure and having an air transport rate of 100–20,000 Gurley seconds (Gs) and (ii) a thickness in the range of from about 0.01 mils up to about 20 mils; and (c) a non-porous containment means removably enclosing said filled porous polymer section and located outwardly from the said outer surface of said filled porous polymer shell section, the removal of said non-porous containment means causing the commencement of functional operation of said structure and the presence of said non-porous containment means preventing said functional operation when said non-porous containment means encloses said filled porous polymer section on its outer surface said microporous polymer shell section having a porosity such that when said hollow totally enclosed structure is located in the ambient environment at a point in time substantially immediately or subsequent to the commencement of functional operation of said structure and thereafter in a controllable time release manner, said volatile material molecules are transported at a substantially constant mass flow rate both of the individual volatile components and totally through said microporous polymer shell section, said microporous polymer shell section consisting essentially of a polyolefin intimately admixed with a powder having an average particle diameter of from about 0.3 up to about 500 microns, said powder being a filler material incompatible with said polymer, said powder being in a proportion of about 5 to 100 parts by weight per 100 parts by weight of polymer, the said volatile composition having a volatility at ambient conditions which is higher than the transmissibility of said microporous polymer shell section, and (ii) located within said inner void on said base portion of said thin shell, said volatile consumable material releasably entrapped in a gel.

8. The hollow totally enclosed structure of claim 7 wherein the thickness of the microporous polymer shell section is about 100 micrometers; the pore size is approximately 0.1 micrometers; the void volume of the polypropylene is approximately 34 cubic centimeters per 100 grams and the density is approximately 900 kilograms per cubic meter.

9. A structure comprising (a) a first hollow totally enclosed structure defined according to claim 7 and enclosing said first structure, (b) a second air-tight totally enclosed structure, said first totally enclosed structure having a volume less than said second air-tight totally enclosed structure, said first totally enclosed structure being of such dimensions that it is (i) enclosable within said second air-tight totally enclosed hollow structure, and (ii) the internal volume of said second air-tight totally enclosed hollow structure is greater than the external volume of said first hollow totally enclosed structure.

10. A structure defined according to claim 7 wherein (i) said base portion comprises a first thin polymer shell having a curved surface and an outer surface and a first sealable continuous circumferential edge; (ii) said upper portion comprises a second thin shell section having a second sealable continuous circumferential edge which substantially conforms in shape to said first sealable circumferential edge and (iii) said base portion is sealed by means of a continuous seal at the said first circumferential edge thereof to said upper portion at the said second circumferential edge thereof.

11. A plurality of hollow totally enclosed structures laterally and detachably interconnected having a common midplane, each of said structures being defined individually according to claim 10, each of said structures connected to at least one other of said structures (i) at a location midway between the base portion of each of said structures and the upper portion of each of said structures and (ii) along at least a portion of the circumferential sealed edge of each of said individual structures sealing said upper portion to said base portion of each of said individual hollow totally enclosed structures.

12. A process for providing an environment with a consumable material selected from the group consisting of perfume compositions, herbicide compositions, insecticide compositions, animal repellent compositions, air freshener compositions, pheromone compositions, odor maskant compositions, deodorant compositions, insect repellent compositions and compositions for the evaluation of olfactory functioning in humans comprising the steps of (i) placing a hollow totally enclosed structure capable of controllable functional operation for the controlled release into the space surrounding said structure of at least one of said consumable materials comprising (1) a thin shell totally enclosing an inner void, said thin shell having an inner surface and an outer surface, the inner surface thereof being the boundary of said inner void, said thin shell having a base portion and an upper portion, said base portion having an inner surface:

(a) contained totally within the inner void of said thin shell and in place on said inner surface of said base portion, a volatile composition existing in the liquid state at ambient conditions temporarily entrapped and totally entrapped in an entrapment material at least at the instant in time of commencement of functional operation of said structure, said volatile composition being selected from the group consisting of perfume compositions, herbicide compositions, insecticide compositions, animal repellent compositions, air freshener compositions, pheromone compositions, odor maskant compositions, deodorant compositions, insect repellent compositions and compositions for the evaluation of olfactory functioning in humans;

(b) at least a finite section of said thin shell section consisting of a filled microporous polymer section consisting essentially of a porous polymer lamina and in random admixture with said polymer lamina a filler dispersed in the pores of said polymer lamina, said filler being in the solid phase, the filler being in a phase separate from the polymer phase of the polymeric lamina, having an inner surface and an outer surface, and having the property of transporting water vapor at a rate of between about 50 $g/m^2/day$ up to about 1000 $g/m^2/day$ at about 25° C. and about 50% relative humidity at about atmospheric pressure and having an air transport rate of 100–20,000 Gurley seconds (Gs) and a thickness in the range of from about 0.01 mils up to about 20 mils; and (c) a non-porous containment means removably enclosing said filled porous polymer section and located outwardly from the said outer surface of said filled porous polymer shell section, the removal of said non-porous containment means causing the commencement of functional operation of said structure and the presence of said non-porous containment means preventing said functional operation when said non-porous containment means encloses said filled porous polymer section on its outer surface said microporous polymer shell section having a porosity such that when said hollow totally enclosed structure is located in the ambient environment at a point in time substantially immediately or subsequent to the commencement of functional operation of said structure and thereafter in a controllable time release manner, said volatile material molecules are transported at a substantially constant mass flow rate both of the individual volatile components and totally through said microporous polymer shell section, and (2) located within said inner void on said base portion of said thin shell, said consumable material releasably entrapped in a gel, in said environment; (ii) removing the non-porous containment means enclosing said filled porous polymeric section from the said filled porous polymeric section; and (iii) permitting the resulting system to equilibrate.

* * * * *